(12) United States Patent
Riedel et al.

(10) Patent No.: US 10,544,115 B2
(45) Date of Patent: Jan. 28, 2020

(54) PROCESS FOR THE PREPARATION OF PROPYLENE OXIDE

(71) Applicant: BASF SE, Ludwigshafen am Rhein (DE)

(72) Inventors: Dominic Riedel, Ludwigshafen (DE);
Joaquim Henrique Teles, Ludwigshafen (DE); Heiner Schelling, Ludwigshafen (DE); Ulrike Wegerle, Worms (DE); Ulrich Mueller, Ludwigshafen (DE); Andrei-Nicolae Parvulescu, Ludwigshafen (DE); Jochen Mannweiler, Ludwigshafen (DE); Timo Henn, Ludwigshafen (DE); Thomas Luederitz, Ludwigshafen (DE); Nicolai Tonio Woerz, Ludwigshafen (DE); Christian Mueller, Ludwigshafen (DE); Markus Weber, Ludwigshafen (DE); Daniel Urbanczyk, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/076,600

(22) PCT Filed: Feb. 16, 2017

(86) PCT No.: PCT/EP2017/053492
§ 371 (c)(1),
(2) Date: Aug. 8, 2018

(87) PCT Pub. No.: WO2017/140774
PCT Pub. Date: Aug. 24, 2017

(65) Prior Publication Data
US 2019/0077779 A1 Mar. 14, 2019

(30) Foreign Application Priority Data

Feb. 17, 2016 (EP) .................................. 16156112

(51) Int. Cl.
*C07D 301/12* (2006.01)
*C07D 301/36* (2006.01)
(Continued)

(52) U.S. Cl.
CPC ........ *C07D 301/12* (2013.01); *B01J 19/0013* (2013.01); *B01J 29/7088* (2013.01);
(Continued)

(58) Field of Classification Search
CPC .. C07D 301/12; C07D 301/36; C07D 303/04; B01J 29/7088; B01J 19/0013;
(Continued)

(56) References Cited

U.S. PATENT DOCUMENTS 5,194,675 A    3/1993  Joerg et al.
2016/0176835 A1    6/2016  Riedel et al.

FOREIGN PATENT DOCUMENTS

EP    0 427 062 A2    5/1991
EP    1 122 249 A1    8/2001
(Continued)

OTHER PUBLICATIONS

U.S. Pat. No. 9,988,268, Jun. 5, 2018, 2017-0197830, Riedel et al.
(Continued)

*Primary Examiner* — Taylor V Oh
(74) *Attorney, Agent, or Firm* — Oblon, McClelland, Maier & Neustadt, L.L.P.

(57) ABSTRACT

A continuous process for the preparation of propylene oxide, comprising a start-up stage and normal run stage, wherein the normal run stage comprises (i) continuously providing a liquid feed stream comprising propene, hydrogen peroxide,
(Continued)

Figure 1:
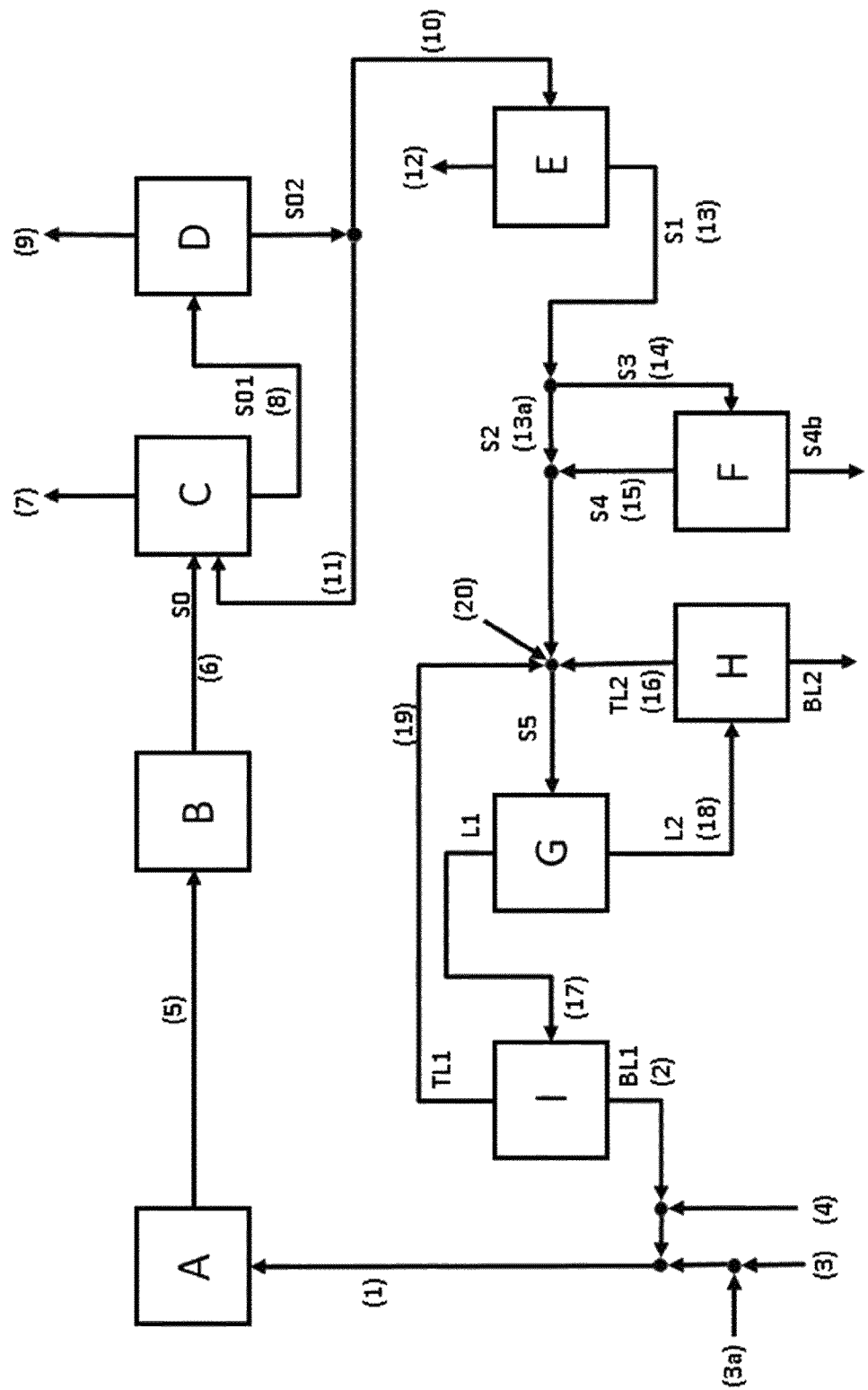

acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$; (ii) continuously passing the liquid feed stream provided in (i) into an epoxidation zone comprising a catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane; (iii) continuously removing an effluent stream from the epoxidation zone, the effluent stream comprising propylene oxide, acetonitrile, water, at least a portion of the formate salt, optionally propene, and optionally propane; wherein the normal run stage is characterized in an average rate of change of $a^N(Fo/H_2O_2)$ of less than $0\ h^{-1}$.

20 Claims, 2 Drawing Sheets

(51) Int. Cl.
  *B01J 19/00* (2006.01)
  *B01J 29/70* (2006.01)
  *C07D 303/04* (2006.01)
(52) U.S. Cl.
  CPC ... *C07D 301/36* (2013.01); *B01J 2219/00033* (2013.01); *B01J 2219/00051* (2013.01); *B01J 2219/00162* (2013.01); *B01J 2219/00166* (2013.01); *C07D 303/04* (2013.01)
(58) Field of Classification Search
  CPC .............. B01J 2219/166; B01J 2219/51; B01J 2219/162; B01J 2219/33
  USPC ........................................................ 549/531
  See application file for complete search history.

(56) References Cited

FOREIGN PATENT DOCUMENTS

WO  WO 2011/006990 A1  1/2011
WO  WO 2015/010990 A1  1/2015

OTHER PUBLICATIONS

U.S. Appl. No. 15/509,238, filed Oct. 5, 2017, 2017-0283352, Fenlon et al.
U.S. Appl. No. 15/509,228, filed Sep. 28, 2017, 2017-0275225, Riedel et al.
U.S. Appl. No. 15/121,940, filed Mar. 9, 2017, 2017-0066882, Mueller et al.
U.S. Pat. No. 9,765,003, Sep. 19, 2017, 2017-0183280, Vautravers et al.
U.S. Pat. No. 9,796,654, Oct. 24, 2017, 2017-0107168, Vautravers et al.
U.S. Appl. No. 15/315,636, filed Jul. 5, 2018, 2018-0186648, Feyen et al.
U.S. Appl. No. 15/509,527, filed Aug. 31, 2017, 2017-0246620, Parvulescu et al.
U.S. Appl. No. 15/305,556, filed Feb. 16, 2017, 2017-0044421, Parvulescu et al.
U.S. Appl. No. 15/305,549, filed Feb. 9, 2017, 2017-0037296, Kimura et al.
U.S. Appl. No. 15/129,222, filed Jun. 28, 2018, 2018-0178191, Schwab et al.
U.S. Appl. No. 15/315,143, filed Aug. 2, 2018, 2018-0215694, Riedel et al.
U.S. Appl. No. 15/550,581, filed Feb. 8, 2018, 2018-0036723, Riedel et al.
U.S. Appl. No. 15/557,187, filed Feb. 15, 2018, 2018-0044179, Schelling et al.
U.S. Pat. No. 9,446,390, Sep. 20, 2016, 2015-0343431, Parvulescu et al.
U.S. Appl. No. 15/316,220, filed May 17, 2018, 2018-0134570, Maurer et al.
U.S. Pat. No. 9,593,065, Mar. 14, 2017, 2016-0031789, Schultz et al.
U.S. Appl. No. 15/549,905, filed Jan. 25, 2018, 2018-0022611, Feyen et al.
U.S. Pat. No. 9,540,305, Jan. 10, 2017, 2015-0344394, Parvulescu et al.
U.S. Appl. No. 15/752,991, filed Aug. 30, 2018, 2018-0243691, Mueller et al.
U.S. Appl. No. 15/518,945, filed Aug. 10, 2017, 2017-0225959, Maurer et al.
U.S. Appl. No. 15/524,484, filed Nov. 23, 2017, 2017/0336030, Weickert et al.
U.S. Appl. No. 15/779,218, filed May 25, 2018, Maurer et al.
U.S. Pat. No. 9,969,708, May 15, 2018, 2017-0320847, Vautravers et al.
U.S. Pat. No. 10,087,395, Oct. 2, 2018, 2017-0362532, Pelzer et al.
U.S. Pat. No. 9,528,223, Dec. 27, 2016, 2015-0337492, Uymur et al.
U.S. Appl. No. 15/514,902, filed Aug. 16, 2018, 2018-0230076, Thrun et al.
U.S. Appl. No. 15/508,725, filed Sep. 28, 2017, 2017-0275076, Edgington et al.
U.S. Pat. No. 9,546,123, Jan. 17, 2017, 2016-0176797, Brueggemann et al.
U.S. Appl. No. 15/521,924, filed Aug. 16, 2018, 2018-0230117, Teles et al.
U.S. Pat. No. 9,695,099, Jul. 4, 2017, 2016-0152541, Liu et al.
U.S. Appl. No. 15/537,128, filed Sep. 20, 2018, 2018-0265443, Vautravers et al.
U.S. Appl. No. 15/,744,324, filed Jul. 26, 2018, 2018-0208532, Parvulescu et al.
U.S. Appl. No. 15/744,474, filed Jul. 26, 2018, 2018-0208533, Ruedenauer et al.
U.S. Appl. No. 15/571,107, filed Jun. 21, 2018, 2018-0170850, Vautravers et al.
U.S. Appl. No. 15/746,183, filed Jul. 26, 2018, 2018-0208745, Vautravers et al.
U.S. Appl. No. 15/779,314, filed May 25, 2018, Burckhart et al.
U.S. Appl. No. 15/746,082, filed Aug. 2, 2018, 2018-0215724, Gordillo et al.
U.S. Appl. No. 16/060,260, filed Jun. 7, 2018, Vautravers et al.
U.S. Pat. No. 9,771,314, Sep. 26, 2017, 2017-0129841, Hartmann et al.
U.S. Appl. No. 15/766,425, filed Apr. 6, 2018, Thrun et al.
U.S. Appl. No. 15/766,407, filed Oct. 11, 2018, 2018-0290959, Thrun et al.
U.S. Pat. No. 9,738,583, Aug. 22, 2017, 2017-0129840, Hartmann et al.
U.S. Appl. No. 15/775,657, filed May 18, 2018, Weickert et al.
U.S. Appl. No. 16/060,739, filed Jun. 8, 2018, Feyen et al.
U.S. Appl. No. 16/060,229, filed Jun. 7, 2018, Parvulescu et al/
U.S. Appl. No. 15/348,217, filed May 11, 2017, 2017-0128916, Lejkowski et al.
International Search Report dated May 8, 2017 in PCT/EP2017/053492.
"Hydrogen Peroxide", Ullmann's Encyclopedia of Industrial Chemistry, $5^{th}$ edition, vol. A 13: High-Performance Fibers to Imidazole and Derivatives, 1989, pp. 443-466 and cover pages.

PROCESS FOR THE PREPARATION OF PROPYLENE OXIDE

The present invention relates to a continuous process for the preparation of propylene oxide which comprises a start-up stage and, after the start-up stage, a normal run stage, wherein the feed stream which is passed to epoxidation comprises a formate salt and hydrogen peroxide, and wherein during the normal run stage, the average rate of change of the molar amount of the formate salt relative to the molar amount of hydrogen peroxide in said feed stream is less than 0 per hour.

Propylene oxide is an important intermediate in the chemical industry. A suitable process for the preparation of propylene oxide starts from propene and makes use of hydrogen peroxide as oxidizing agent, acetonitrile as solvent and a heterogeneous zeolitic epoxidation catalyst having framework type MWW and containing titanium. Due to its importance for industrial-scale processes, it is desired to carry out this epoxidation reaction as efficiently as possible WO 2015/010990 A discloses a continuous process for the preparation of propylene oxide, wherein this process comprises providing a liquid feed stream comprising propene, hydrogen peroxide, acetonitrile, water, optionally propane, and at least one dissolved potassium salt. According to WO 2015/010990 A, it was found that the presence of at least one dissolved potassium salt in the liquid feed stream provided in (i) allows for an excellent epoxidation performance of the epoxidation catalyst used in the process, which catalyst comprises a titanium zeolite having framework type MWW. Yet further, it was found that excellent epoxidation characteristics in terms of hydrogen peroxide conversion and propylene oxide selectivity were achieved if organic potassium salts are employed. With regard to specific amounts of the dissolved potassium salt, WO 2015/010990 A teaches that the concentration of the potassium salt in the liquid feed stream is not subject to any specific restrictions, and that it is preferred that the concentration of the dissolved potassium salt in the liquid feed stream provided in (i) is at least 10%, preferably in the range of from 10 to 100%, preferably from 20 to 100%, more preferably from 30 to 100%, more preferably from 40 to 100% of the solubility limit of the potassium salt in the liquid feed stream provided in. According to the examples of WO 2015/010990 A, the concentration of the potassium salt is kept constant at a specific value during the continuous epoxidation reaction.

It was an object of the present invention to provide a continuous process for the preparation of propylene oxide which is even more efficient than the process described in WO 2015/010990 A, in particular if the process is carried out in an industrial scale.

Surprisingly, it was found that if in the course of the normal run stage of a continuous process for the preparation of propylene oxide, the amount of a formate salt relative to the amount of hydrogen peroxide in the liquid feed stream subjected to epoxidation conditions is specifically varied so that at the end of the normal run stage of the continuous process, the molar amount of the formate salt relative to the molar amount of hydrogen peroxide is lower that the molar amount of the formate salt relative to the molar amount of hydrogen peroxide at the beginning of the normal run stage, the selectivity of the process relative to the valuable product propylene oxide can be positively influenced. More surprisingly, it was found that these advantageous results with respect to the selectivity were obtained even in such cases when, during the normal run stage, the epoxidation temperature was slightly increased in order to achieve a constant hydrogen peroxide conversion, although according the skilled person's expectations, a temperature increase should result in a negative influence on the selectivity to the valuable product. Thus, it was found that although the concentration of the formate salt in the liquid feed stream was decreased in the course of the normal run stage, the selectivity to the valuable product were increased and the selectivities to undesired by-products such as oxygen and methoxypropylene glycol (MPG) were decreased. Yet further, it was found that by using the process set-up of the present invention, extremely long normal run stages and, thus, extremely long lifetimes of the epoxidation catalyst used can be achieved.

Therefore, the present invention relates to a continuous process for preparing propylene oxide comprising a normal run stage and a start-up stage, wherein the normal run stage comprises (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$;

(ii) continuously passing the liquid feed stream provided in (i) into an epoxidation zone comprising a catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;

(iii) continuously removing an effluent stream from the epoxidation zone, the effluent stream comprising propylene oxide, acetonitrile, water, at least a portion of the formate salt, optionally propene, and optionally propane;

wherein the normal run stage is characterized in an average rate of change of $a^N(Fo/H_2O_2)$ of less than 0 $h^{-1}$.

The term "optionally propane" describes that propene as the starting material is either used as pure propene or as a mixture of propene and propane. If a mixture of propene and propane is used in (i), the reaction mixture in (ii) and the effluent stream in (iii) contain propane.

The term "normal run stage" according to the present invention describes the period of time between the start-up stage of the continuous process and the end of the continous process. The start-up stage of the process is generally characterized in that individual streams comprising propene and optionally propane, comprising hydrogen peroxide, comprising acetonitrile, and comprising the formate salt, are suitably and sequentially admixed until a predetermined composition of the resulting stream is obtained which is the liquid feed stream according to (i) at the beginning of the normal run stage; during the start-up process, the concentration of the hydrogen peroxide in the stream resulting from mixing the above-mentioned individual streams is preferably suitably increased wherein, when the pre-determined maximum concentration is reached, the start-up stage is over and the normal run stage begins. The end of of the continuous process is defined when by any suitable means, the epoxidation reaction in the epoxidation reaction zone is interrupted, for example by stopping the addition of hydrogen peroxide when providing the liquid feed stream in (i) or the like.

Normal Run Stage

Step (i)

The term "average rate of change of $a^N(Fo/H_2O_2)$" as used in the context of the present invention is defined as $[a^N(Fo/H_2O_2)(t_{max})-a^N(Fo/H_2O_2)(t_0)]/[t_{max}-t_0]$, wherein $[t_{max}-t_0]$ is the duration of the normal run stage defined by difference from the end point of the normal run stage at a time $t_{max}$ and the start point of the normal run stage at a time $t_0$, wherein $a^N(Fo/H_2O_2)(t_{max})$ is the value of $a^N(Fo/H_2O_2)$ at the time $t_{max}$ and wherein $a^N(Fo/H_2O_2)(t_0)$ is the value of $a^N(Fo/H_2O_2)$ at the time $t_0$.

Therefore, the present invention also relates to a continuous process for preparing propylene oxide comprising a normal run stage and a start-up stage, wherein the normal run stage comprises (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$;

(ii) continuously passing the liquid feed stream provided in (i) into an epoxidation zone comprising a catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;

(iii) continuously removing an effluent stream from the epoxidation zone, the effluent stream comprising propylene oxide, acetonitrile, water, at least a portion of the formate salt, optionally propene, and optionally propane;

wherein the normal run stage is characterized in an average rate of change of $a^N(Fo/H_2O_2)$ of less than 0 $h^{-1}$ wherein the average rate of change of $a^N(Fo/H_2O_2)$ is defined as $[a^N(Fo/H_2O_2)(t_{max})-a^N(Fo/H_2O_2)(t_0)]/[t_{max}-t_0]$, wherein $[t_{max}-t_0]$ is the duration of the normal run stage defined by difference from the end point of the normal run stage at a time $t_{max}$ and the start point of the normal run stage at a time $t_0$, wherein $a^N(Fo/H_2O_2)(t_{max})$ is the value of $a^N(Fo/H_2O_2)$ at the time $t_{max}$ and wherein $a^N(Fo/H_2O_2)(t_0)$ is the value of $a^N(Fo/H_2O_2)$ at the time $t_0$.

Preferably, during the normal run stage, the value of $a^N(Fo/H_2O_2)$ at a given time $(t_2-t_0)$, $a^N(Fo/H_2O_2)(t_2-t_0)$, is less than or equal to the value of $a^N(Fo/H_2O_2)$ at a given time $t_1-t_0$, $a^N(Fo/H_2O_2)(t_1-t_0)$, wherein $(t_2-t_0)$ is greater than $(t_1-t_0)$, provided that at the end of the normal run stage, at the time $t_{max}$, the average rate of change of $a^N(Fo/H_2O_2)$ of less than 0 $^{-1}$. Therefore, it is preferred that during the normal run stage, the value of $a^N(Fo/H_2O_2)$ is either kept constant for a certain period of time or decreased for a certain period of time provided that at the end of the normal run stage, $a^N(Fo/H_2O_2)(t_{max})$ is smaller than $a^N(Fo/H_2O_2)(t_0)$.

Therefore, the present invention also relates to a continuous process for preparing propylene oxide comprising a normal run stage and a start-up stage, wherein the normal run stage comprises (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$;

(ii) continuously passing the liquid feed stream provided in (i) into an epoxidation zone comprising a catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;

(iii) continuously removing an effluent stream from the epoxidation zone, the effluent stream comprising propylene oxide, acetonitrile, water, at least a portion of the formate salt, optionally propene, and optionally propane;

wherein the normal run stage is characterized in an average rate of change of $a^N(Fo/H_2O_2)$ of less than 0 $^{-1}$ wherein the average rate of change of $a^N(Fo/H_2O_2)$ is defined as $[a^N(Fo/H_2O_2)(t_{max})-a^N(Fo/H_2O_2)(t_0)]/[t_{max}-t_0]$, wherein $[t_{max}-t_0]$ is the duration of the normal run stage defined by difference from the end point of the normal run stage at a time $t_{max}$ and the start point of the normal run stage at a time $t_0$, wherein $a^N(Fo/H_2O_2)(t_{max})$ is the value of $a^N(Fo/H_2O_2)$ at the time $t_{max}$ and wherein $a^N(Fo/H_2O_2)(t_0)$ is the value of $a^N(Fo/H_2O_2)$ at the time $t_0$, and wherein $a^N(Fo/H_2O_2)(t_2-t_0)$ is smaller than or equal to $a^N(Fo/H_2O_2)(t_1-t_0)$, wherein $(t_2-t_0)$ is greater than $(t_1-t_0)$, wherein $t_0<t_1<t_{max}$ and $t_0<t_2<t_{max}$.

Preferably, the average rate of change of $a^N(Fo/H_2O_2)$ is in the range of from $-10^{-10}$ to $-10^{-6}$ $h^{-1}$, more preferably in the range of from $-10^{-9}$ to $-10^{-7}$ $h^{-1}$, such as in the range of from $-10^{-9}$ to $-10^{-8}$ $h^{-1}$ or in the range of from $-10^{-8}$ to $-10^{-7}$ $h^{-1}$. Preferably, at the beginning of the normal run stage, at the time $t_0$, $a^N(Fo/H_2O_2)$ is in the range of from $1.0*10^{-4}$ to $1.0*10^{-2}$, more preferably in the range of from $5.0*10^{-4}$ to $1.0*10^{-3}$, such as in the range of from $6.0*10^{-4}$ to $9.0*10^{-4}$ or in the range of from $7.0*10^{-4}$ to $8.0*10^{-4}$. Therefore, it is preferred that the average rate of change of $a^N(Fo/H_2O_2)$ is in the range of from $-10^{-10}$ to $-10^{-6}$ $h^{-1}$ and $a^N(Fo/H_2O_2)(t_0)$ is in the range of from $1.0*10^{-4}$ to $1.0*10^{-2}$. More preferably, the average rate of change of $a^N(Fo/H_2O_2)$ is in the range of from $-10^{-9}$ to $-10^{-7}$ $h^{-1}$ and $a^N(Fo/H_2O_2)(t_0)$ is in the range of from $5.0*10^{-4}$ to $1.0*10^{-3}$.

Preferably, the formate salt according to (i) is one or more an alkali metal formate salts, one or more alkaline earth metal formate salts, or a mixture of one or more alkali metal formate salts and one or more alkaline earth metal formate salts. More preferably, the formate salt according to (i) comprises one or more alkali metal formate salts, more preferably comprises a potassium formate salt. More preferably, the formate salt according to (i) comprises $K^+COO^-$. More preferably, the formate salt according to (i) is $K^+COO^-$.

Generally, the composition of the liquid feed stream provided in (i) is not subject to any specific restrictions. Preferably, during the normal run stage, the liquid feed stream provided in (i) comprises the acetonitrile in an amount in the range of from 60 to 75 weight-%, preferably in the range of from 60 to 65 weight-%, based on the total weight of the liquid feed stream;

the hydrogen peroxide in an amount in the range of from 6 to 10 weight-%, preferably in the range of from 7 to 9 weight-%, based on the total weight of the liquid feed stream;

the water at a molar ratio of water relative to acetonitrile of at most 1:4, preferably in the range of from 1:50 to 1:4, more preferably in the range of from 1:15 to 1:4.1, more preferably in the range of from 1:10 to 1:4.2;

the propene at a molar ratio of propene relative to hydrogen peroxide comprised in the liquid feed stream in the range of from 1:1 to 1.6:1, preferably in the range of from 1.1:1 to 1.5:1; and optionally the propane at a molar ratio of propane relative to the sum of propene and propane in the range of from 0.0001:1 to 0.15:1, preferably in the range of from 0.001:1 to 0.05:1.

Preferably at least 95 weight-%, more preferably from 95 to 100 weight-%, more preferably from 98 to 100 weight-% of the liquid feed stream provided in (i) consist of propene, hydrogen peroxide, acetonitrile, the formate salt, water and optionally propane.

Preferably, the liquid feed stream provided in (i), preferably passed as the sole feed stream into the epoxidation reactor, is free of ammonium dihydrogen phosphate. More preferably, the liquid feed stream provided in (i), preferably passed as the sole feed stream into the epoxidation reactor, is free of ammonium phosphate, ammonium hydrogen phosphate and ammonium dihydrogen phosphate. More preferably, the liquid feed stream provided in (i), preferably passed as the sole feed stream into the epoxidation reactor, is free of ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate, and ammonium acetate. More preferably, the liquid feed stream provided in (i), preferably passed as the sole feed stream into the epoxidation reactor, is free of an ammonium salt. The term "free of" as used in this context of the present invention relates to a concentration of a respective compound of at most 2 weight-ppm, preferably at most 1 weight-ppm, based on the total weight of the liquid feed stream. Therefore, the present invention also relates to the process as described above, wherein the liquid feed stream provided in (i), preferably passed as the sole feed stream into the epoxidation reactor, contains ammonium $NH_4^+$ in an amount in the range of from 0 to 2 weight-ppm, preferably in the range of from 0 to 1 weight-ppm, based on the total weight of the liquid feed stream.

Preferably, the liquid feed stream provided in (i), preferably passed as the sole feed stream into the epoxidation reactor, contains sodium in a molar ratio of sodium relative to hydrogen peroxide in the range of from $1*10^{-6}:1$ to $250*10^{-6}:1$, preferably in the range of from $5*10^{-6}:1$ to $50*10^{-6}:1$.

Preferably, the liquid feed stream provided in (i), preferably passed as the sole feed stream into the epoxidation reactor, does not comprise dissolved sodium dihydrogen phosphate ($NaH_2PO_4$), more preferably neither dissolved sodium dihydrogen phosphate nor dissolved disodium hydrogen phosphate ($Na_2HPO_4$), more preferably neither dissolved sodium dihydrogen phosphate nor dissolved disodium hydrogen phosphate nor dissolved sodium phosphate ($Na_3PO_4$).

Preferably, the liquid feed stream provided in (i), preferably passed as the sole feed stream into the epoxidation reactor, does not comprise dissolved sodium dihydrogen phosphate ($KH_2PO_4$), more preferably neither dissolved sodium dihydrogen phosphate nor dissolved disodium hydrogen phosphate ($K_2HPO_4$), more preferably neither dissolved sodium dihydrogen phosphate nor dissolved disodium hydrogen phosphate nor dissolved sodium phosphate ($K_3PO_4$).

Generally, the liquid feed stream can be provided in (i) according to any conceivable method. Preferably, the liquid feed stream is provided in (i) by combining at least four individual streams wherein a first stream comprises hydrogen peroxide, a second stream comprises propene and optionally propane, a third stream comprises acetonitrile and optionally water, and a fourth stream comprises the formate salt in an amount so that the formate salt is dissolved in the liquid feed stream provided in (i).

These at least four individual stream can be combined in every suitably order. Preferably, the stream comprising the formate salt is combined with the stream comprising hydrogen peroxide, and the resulting combined stream is combined with a stream which results from combining the stream comprising acetonitrile and the stream comprising propene and optionally propane. The thus obtained stream is the liquid stream provided in (i).

Therefore, the present invention also relates to the process as described above, wherein in (i), the liquid feed stream is provided by combining a stream comprising hydrogen peroxide, a stream comprising acetonitrile and optionally water, and a stream comprising propene and optionally propane, wherein an aqueous stream comprising the formate salt is combined with the stream comprising hydrogen peroxide, or with the stream comprising acetonitrile and optionally water, or with the stream comprising propene and optionally propane, or with a mixed stream of two or three of these streams, preferably with the stream comprising hydrogen peroxide.

Preferably, the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%. Preferably, the stream comprising propene and optionally propene is free of potassium cations ($K^+$) and free of phosphorus (P) in the form of anions of at least one phosphorus oxyacid. The term "free of potassium cations ($K^+$)" as used in this context of the present invention refers to a stream comprising propene and optionally propane, containing potassium cations ($K^+$) in an amount of less than 1 weight-ppm, preferably less than 0.1 weight-ppm, based on the total weight of the stream. The term "free of phosphorus (P) in the form of anions of at least one phosphorus oxyacid" as used in this context of the present invention refers to a stream comprising propene and optionally propane, containing phosphorus (P) in the form of anions of at least one phosphorus oxyacid in an amount of less than 1 weight-ppm, preferably less than 0.1 weight-ppm, based on the total weight of the stream. It is conceivable that in addition to the stream comprising propene and optionally propane which is used for providing the liquid feed stream in (i), a further stream comprising propene and optionally propane may be employed. This further stream is preferably formed in a step (iv) of the present invention described hereinbelow, wherein the epoxidation mixture removed according to (iii) is subjected to distillation. In step (iv), in addition to the bottoms stream comprising propylene oxide, acetonitrile and water and being depleted of propene and optionally propane, a distillation top stream is obtained being enriched in propene and optionally propane. This top stream, optionally after work-up, can be recycled to the epoxidation reaction as part of the liquid feed stream provided in (i). The volume ratio of the fresh stream comprising propene and optionally propane relative to the recycled stream comprising propene and optionally propane is in the range of from 0.1:1 to 20:1, preferably from 1:1 to 10:1, more preferably from 2:1 to 5:1.

While it is conceivable that during the normal run stage, the stream comprising acetonitrile which is used for providing the liquid feed stream in (i) is a stream of fresh acetonitrile, it is preferred that the stream comprising acetonitrile which is used for providing the liquid feed stream in (i) at least partially, preferably essentially consists of a recycled acetonitrile stream resulting from the work-up of the effluent stream which is removed in (iii) from the epoxidation reactor and which comprises propylene oxide, acetonitrile, water, at least a portion of the formate salt, optionally propene, and optionally propane. During the work-up of the effluent stream, it is preferred to remove essentially all compounds other than acetonitrile and water from the stream and recycle the thus purified stream back to the epoxidation reaction. According to a preferred work-up of the present invention, the stream comprising propene and optionally propane as described above is combined with the acetonitrile recycle stream, either after the final purification stage of the acetonitrile recycle stream or before the final purification stage or final purification stages of the acetonitrile recycle stream. Preferably, the stream comprising propene and optionally propane as described above is combined with the acetonitrile recycle stream before the final purification stages, more preferably before a work-up stage where a stream comprising acetonitrile and water is subjected to a phase separation, preferably a liquid-liquid phase separation and where this phase separation is carried out using the stream comprising propene and optionally propane as separation-promoting compound. Optionally, after this separation stage, the resulting acetonitrile recycle stream, now additionally containing propene and optionally propane, can be subjected to further purification. An especially preferred work-up of the effluent stream removed according to step (iii) is described in detail hereinbelow. Preferably, the acetonitrile recycle stream to which the stream comprising propene and optionally comprising propane had been added and which had been preferably subjected to phase separation and optional further purification has a composition of which preferably at least 98 weight-%, more preferably at least 99 weight-%, more preferably at least 99.5 weight-% consist of acetonitrile, water, and propene. More preferably, at least 75 weight-%, more preferably in the range of from 75 to 90 weight-%, more preferably from 80 to 85 weight-% of the recycle stream consist of acetonitrile and water. In the recycle stream, the molar ratio of acetonitrile relative to water is preferably at most 1:9, more preferably in the range of from 1:50 to 1:9, preferably from 1:25 to 1:9, more preferably from 1:25 to 1:10. A preferred process for working up the effluent stream and recycling the acetonitrile is described hereinbelow.

For starting the continuous process of the present invention and for compensating any losses of acetonitrile in the course of the work-up of the effluent stream obtained in (iii), a part of the stream comprising acetonitrile used for providing the liquid feed stream in (i) can be a make-up acetonitrile stream. Preferably, the make-up acetonitrile stream is a chemical grade acetonitrile stream having an acetonitrile content of preferably at least 99.5 weight-%, more preferably at least 99.7 weight-%, more preferably at least 99.8 weight-%. Preferably, during the continuous process of the present invention, the weight ratio of the recycled acetonitrile stream relative to the make-up acetonitrile stream is in the range of from 1000:1 to 100:1, preferably from 950:1 to 300:1, more preferably from 900:1 to 500:1.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight % or from 35 to 75 weight-% or from 40 to 70 weight-%.

According to the present, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5th edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/reoxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution.

In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1

122 249 A1. As to the term "essentially pure water", reference is made to paragraph 10, page 3 of EP 1 122 249 A1 which is incorporated by reference.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1 \times 10^{-6}:1$ to $250 \times 10^{-6}:1$, more preferably from $5 \times 10^{-6}:1$ to $50 \times 10^{-6}:1$.

Therefore, the present invention relates to the process as defined above, wherein wherein the stream comprising hydrogen peroxide is an aqueous hydrogen peroxide stream having a hydrogen peroxide concentration in the range of from 25 to 75 weight-%, preferably from 30 to 50 weight-%, based on the total weight of the aqueous hydrogen peroxide stream, wherein the aqueous hydrogen peroxide stream further comprises sodium with a molar ratio of sodium relative to hydrogen peroxide in the range of from $1*10^{-6}:1$ to $250*10^{-6}:1$, preferably from $5*10^{-6}:1$ to $50*10^{-6}:1$.

Preferably, during the normal run stage, the temperature of the liquid feed stream provided in (i) is in the range of from 0 to 60° C., more preferably in the range of from 10 to 55° C., more preferably in the range of from 25 to 50° C. Preferably, the liquid feed stream provided in (i) and passed into the epoxidation zone in (ii) is at a pressure in the range of from 14 to 100 bar(absolute), more preferably from 14.5 to 50 bar(absolute), more preferably from 15 to 25 bar (absolute). Therefore, the present invention relates to the process as described above, wherein during the normal run stage, the liquid feed stream provided in (i) and passed into the epoxidation zone in (ii) has a temperature in the range of from 0 to 60° C., preferably in the range of from 25 to 50° C., and is at a pressure in the range of from 14 to 100 bar, preferably in the range of from 15 to 25 bar.

Step (ii)

According to (ii), the liquid feed stream provided in (i) is passed into an epoxidation zone. Generally, there are no specific restrictions regarding the design of the epoxidation zone provided that it is suitable for carrying out a continuous epoxidation reaction. Preferably, the epoxidation zone according to (ii) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a continuous epoxidation reaction.

Preferably, the epoxidation zone according to (ii) comprises a first epoxidation subzone consisting of one or more epoxidation reactors A. The term "first epoxidation subzone" as used in this context of the present invention relates to the epoxidation subzone into which the liquid feed stream provided in (i) is passed, wherein the epoxidation zone of (ii) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (ii), the liquid feed stream provided in (i) is passed into at least one of the epoxidation reactors A. It is possible, for example, that, while the liquid feed stream provided in (i) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor.

During the normal run stage, it is preferred that the epoxidation conditions according to (ii) comprise an epoxidation temperature $T^N$ wherein the average rate of change of $T^N$ is in the range of from 0 to 50 $K*h^{-1}$. $T^N$ is the temperature of a heat transfer medium used for adjusting the temperature of the reaction mixture in the first epoxidation reaction subzone according to (ii) wherein it is preferred that said temperature is adjusted by passing the heat transfer medium through a jacket of the one or more epoxidation reactors A, wherein $T^N$ is preferably the temperature of the heat transfer medium prior to adjusting the temperature of the reaction mixture, preferably the temperature of the heat transfer medium at the entrance of the jacket of the one or more epoxidation reactors A. If the first epoxidation subzone comprises two or more epoxidation reactors A, the epoxidation temperature $T^N$ relates to the epoxidation temperature $T^N$ of a given reactor A in operation of first epoxidation subzone.

Preferably, during the normal run stage, the average rate of change of $T^N$ is in the range of from 0 to 40 $K*h^{-1}$, preferably in the range of from 0 to 30 $K*h^{-1}$, more preferably in the range of from 0 to 30 $K*h^{-1}$. The term "average rate of change of $T^N$" is defined as $[T^N(t_{max})-T^N(t_0)]/[t_{max}-t_0]$, wherein $[t_{max}-t_0]$ is the duration of the normal run stage defined by the difference from the end point of the normal run stage at a time $t_{max}$ and the start point of the normal run stage at a time $t_0$, wherein $T^N(t_{max})$ is the value of $T^N$ at the time $t_{max}$ and wherein $T^N(t_0)$ is the value of $T^N$ at the time $t_0$.

Preferably, during the initial stage of the normal run stage, the average rate of change of $T^N$ is in the range of from 0 to 0.5 $K*h^{-1}$, more preferably in the range of from 0 to 0.2 $K*h^{-1}$, more preferably in the range of from 0 to 0.1 $K*h^{-1}$, and wherein, after said initial stage, $T^N$ is increased by at least 0.1° C., preferably by at least 0.5° C., preferably by at least 1° C. The term "initial stage of the normal run stage" is defined as the period of time, starting at $t=t_0$, when at a given point of time t of this period of time, $a^N(Fo/H_2O_2)(t)$ is in the range of from 40 to 60%, preferably 45 to 55% of $a^N(Fo/H_2O_2)(t_0)$.

Preferably, during the normal run stage, $T^N$ is in the range of from 20 to 70° C., more preferably in the range of from 25 to 65° C., more preferably in the range of from 30 to 60° C.

During the normal run stage, it is preferred that the epoxidation conditions according to (ii) comprise a first epoxidation reaction pressure in the range of from 14 to 100 bar, more preferably in the range of from 15 to 32 bar, more preferably in the range of from 15 to 25 bar. The first epoxidation reaction pressure is defined as the absolute pressure at the exit of the first epoxidation subzone. If the first epoxidation subzone comprises two or more epoxidation reactors A, the first epoxidation reaction pressure relates to the absolute pressures at the exit of a given reactor A in operation of first epoxidation subzone.

During the normal run stage, it is preferred that the epoxidation conditions according to (ii) comprise a catalyst loading in the first epoxidation subzone in the range of from 0.05 to 1.25 $h^{-1}$, more preferably in the range of from 0.1 to 1 $h^{-1}$, more preferably in the range of from 0.2 to 0.7 $h^{-1}$, wherein the catalyst loading is defined as the ratio of the mass flow rate in kg/h of hydrogen peroxide contained in liquid feed stream provided in (i) and passed into (ii) relative to the amount in kg of catalyst comprising a titanium zeolite having framework type MWW comprised in the first epoxidation subzone according to (ii). If the first epoxidation subzone comprises two or more epoxidation reactors A, the catalyst loading in the first epoxidation subzone relates to the catalyst loading in a given reactor A in operation of first epoxidation subzone.

According to a first preferred embodiment of the present invention, the epoxidation zone according to (ii) consists the first epoxidation subzone.

According to a second preferred embodiment of the present invention, the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (ii), the effluent stream obtained from the first epoxidation subzone, optionally after a suitable intermediate treatment, is passed into at least one of the epoxidation reactors B. It is possible, for example, that while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (ii) comprises at least one further epoxidation subzone arranged downstream of the second epoxidation subzone.

Preferably, according to the second preferred embodiment of the present invention, the epoxidation zone according to (ii) consists of the first epoxidation subzone and the second epoxidation subzone.

During the normal run stage, it is preferred that the epoxidation conditions according to (ii) comprise a second epoxidation reaction pressure in the range of from 14 to 100 bar, preferably in the range of from 14.5 to 32 bar, more preferably in the range of from 15 to 25 bar. The second epoxidation reaction pressure is defined as the absolute pressure at the exit of the second epoxidation subzone. If the second epoxidation subzone comprises two or more epoxidation reactors B, the second epoxidation reaction pressure relates to the absolute pressures at the exit of a given reactor B in operation of second epoxidation subzone.

During the normal run stage, it is preferred that the epoxidation conditions according to (ii) comprise a catalyst loading in the second epoxidation subzone in the range of from 0.001 to 0.5 $h^{-1}$, more preferably in the range of from 0.005 to 0.3 $h^{-1}$, more preferably in the range of from 0.01 to 0.2 $h^{-1}$, wherein the catalyst loading is defined as the ratio of the mass flow rate in kg/h of of hydrogen peroxide contained in the feed stream passed into the second epoxidation subzone relative to the amount in kg of catalyst comprising a titanium zeolite having framework type MWW comprised in the second epoxidation subzone according to (ii).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

The effluent stream obtained from the first epoxidation subzone, prior to being passed in to the second epoxidation subzone, may be subjected to a suitable intermediate treatment. It is preferred that during such intermediate treatment, the chemical composition of the stream is not changed. More preferably, the intermediate treatment comprises a heat exchange according to which, more preferably, the temperature of the effluent stream obtained from the first epoxidation subzone is decreased before the stream is passed into the second epoxidation subzone. The energy withdrawn from the stream can be used at one or more suitable stages of the overall epoxidation process, for example for increasing the temperature of a suitable process stream.

During the the normal run stage, it is preferred that the epoxidation conditions according to (ii) comprise a hydrogen peroxide conversion $c^N(H_2O_2)$, wherein the average rate of change of $c^N(H_2O_2)$ is in the range of from $-1.0*10^{-3}$ to $1.0*10^{-3}$%-points*$h^{-1}$, wherein $c^N(H_2O_2)$ is defined as the molar amount of hydrogen peroxide comprised in the effluent stream removed in (iii) relative to the molar amount of hydrogen peroxide comprised in the liquid feed stream provided in (i) at a given point of time during the normal run stage, wherein during the normal run stage, $c^N(H_2O_2)$ is preferably in the range of from 80 to 100%, more preferably from 90 to 100%, more preferably from 95 to 100%, more preferably from 99 to 100%, more preferably from 99.5 to 100%. If the epoxidation zone according to (ii) consists of the first epoxidation subzone, the hydrogen peroxide conversion $c^N(H_2O_2)$ is defined as the molar amount of hydrogen peroxide comprised in the effluent stream removed in (iii) from the one or more epoxidation reactors A relative to the molar amount of hydrogen peroxide comprised in the liquid feed stream provided in (i) at a given point of time during the normal run stage. If the epoxidation zone according to (ii) consists of the first epoxidation subzone and the second epoxidation subzone arranged downstream of the first epoxidation subzone, the hydrogen peroxide conversion $c^N(H_2O_2)$ is defined as the molar amount of hydrogen peroxide comprised in the effluent stream removed in (iii) from the one or more epoxidation reactors B relative to the molar amount of hydrogen peroxide comprised in the liquid feed stream provided in (i) at a given point of time during the normal run stage.

Preferably, in the epoxidation zone according to (ii), the reaction mixture is liquid under the epoxidation conditions. More preferably, in the epoxidation zone according to (ii), the reaction mixture consists of one single liquid phase under the epoxidation conditions.

Catalyst

The catalyst comprising the titanium zeolite having framework type MWW can be employed in every conceivable, including a powder, a micropowder, preferably a spray-powder, as a molding comprising a powder, or as a molding comprising a micropowder, preferably a spray-powder. Preferably, the catalyst comprising the titanium zeolite having framework type MWW is employed as a molding comprising a powder or a micropowder, preferably a spray-powder, more preferably as a molding comprising a micropowder, preferably a spray-powder. Regarding a preferred micropowder, reference is made to the micropowder characterized by the respective micropowder embodiments 1 to 14 hereinbelow. Regarding a preferred molding, reference is made to the molding characterized by the respective molding embodiments 1 to 8 hereinbelow. More preferably, the catalyst comprising the titanium zeolite having framework type MWW is present in the epoxidation zone as a molding, preferably as fluidized-bed catalyst or a fixed-bed catalyst, more preferably as a fixed-bed catalyst.

Preferably, the titanium zeolite having framework type MWW comprised in the catalyst according to (ii) contains titanium, calculated as elemental titanium, in an amount in the range of from 0.1 to 5 weight-%, preferably in the range of from 1 to 2 weight-%, based on the total weight of the titanium zeolite having framework type MWW. More preferably, the titanium zeolite having framework type MWW comprised in the catalyst according to (ii) additionally contains zinc, calculated as elemental zinc, in an amount in the range of from 0.1 to 5 weight-%, preferably in the range of from 1 to 2 weight-%, based on the total weight of the titanium zeolite having framework type MWW. Preferably, the catalyst comprising the titanium zeolite having framework type MWW is in the form of a molding, comprising the titanium zeolite having framework type MWW and a binder, preferably a silica binder, wherein the catalyst comprises the titanium zeolite having framework type MWW preferably in an amount in the range of from 70 to 80 weight-%, based on the total weight of the catalyst, and the silica binder preferably in an amount of from 30 to 20 weight-%, based on the total weight of the catalyst, wherein preferably at least 99 weight-% of the catalyst consist of the titanium zeolite having framework type MWW together and the binder.

Said catalyst used according to step (ii) of the present invention, being present in the form of a micropowder comprising the ZnTiMWW, is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). The Dv10 value is understood as being determined according to Reference Example 3.1 of the present invention.

2. The micropowder of embodiment 1, having a Dv10 value in the range of from 2 to 5.5 micrometer, preferably from 3 to 5.5 micrometer.

3. The micropowder of embodiment 1 or 2, having a Dv50 value in the range of from 7 to 25 micrometer and optionally a Dv90 value in the range of from 26 to 85 micrometer. The Dv50 and Dv90 values are understood as being determined according to Reference Example 3.1 of the present invention.

4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.

5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.

6. The micropowder of any of embodiments 1 to 5, wherein the micropores of the ZnTiMWW have an average pore diameter in the range of from 1.0 to 1.2 nanometer as determined by nitrogen adsorption according to DIN 66135.

7. The micropowder of any of embodiments 1 to 6, comprising, based on the weight of the micropowder, at least 99 weight-%, preferably at least 99.7 weight-% of the ZnTiMWW.

8. The micropowder of any of embodiments 1 to 7, wherein the ZnTiMWW contains zinc in an amount of from 1.0 to 2.0 weight-%, preferably of from 1.2 to 1.9 weight-%, calculated as Zn and based on the weight of the ZnTiMWW.

9. The micropowder of any of embodiments 1 to 8, wherein the ZnTiMWW contains titanium in an amount of from 1.0 to 2.0 weight-%, preferably of from 1.2 to 1.8 weight-%, calculated as Ti and based on the weight of the ZnTiMWW.

10. The micropowder of any of embodiments 1 to 9, having a crystallinity, as determined by X-ray diffraction (XRD) analysis, of at least (80+/−10) %, preferably of at least (85+/−10) %. The crystallinity is understood as being determined according to Reference Example 3.7 of the present invention.

11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.

12. The micropowder of any of embodiments 1 to 11, comprising, based on the total weight of the micropowder and calculated as element, less than 0.1 weight.-%, preferably less than 0.01 weight-% of boron.

13. The micropowder of any of embodiments 1 to 12, having a bulk density of in the range of from 80 to 100 g/ml.

14. The micropowder of any of embodiments 1 to 13, being a spray powder, preferably obtainable or obtained by spray-drying.

Further, said catalyst used according to step (ii) of the present invention being present in the form of a molding comprising the ZnTiMWW, is preferably characterized by the following features and embodiments, including the combinations of embodiments according to the given dependencies:

1. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.
2. The molding of embodiment 1, comprising mesopores having an average pore diameter in the range of from 4 to 40 nm, preferably from 20 to 30 nm as determined by Hg porosimetry according to DIN 66133.
3. The molding of embodiment 1 or 2, having a crystallinity, as determined by XRD analysis, of at least (55 +/−10) %, preferably in the range of from ((55 to 75)+/−10) %. The crystallinity is understood as being determined according to Reference Example 3.7 of the present invention.
4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 3.2 of the present invention.
5. The molding of any of embodiments 1 to 4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 3.3 of the present invention.
6. The molding of any of embodiments 1 to 5, the $^{29}$Si-NMR spectrum of said molding comprising six peaks at the following position
   peak 1 at −98+/−x ppm,
   peak 2 at −104+/−x ppm,
   peak 3 at −110+/−x ppm,
   peak 4 at −113+/−x ppm,
   peak 5 at −115+/−x ppm,
   peak 6 at −118+/−x ppm,
   with x in any of the peaks being 1.5, preferably 1.0, more preferably 0.5,
   wherein Q which is defined as
   $Q=100*\{[a_1+a_2]/[a_4+a_5+a_6]\}/a_3$
   is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3. These $^{29}$Si-NMR characteristics are understood as being determined according the Reference Example 3.4 of the present invention.
7. The molding of any of embodiments 1 to 6, having a water uptake in the range of from 3 to 8 weight-%, preferably from 4 to 7 weight-%. The water uptake is understood as being determined according to Reference Example 3.5 of the present invention.
8. The molding of any of embodiments 1 to 7, the infrared spectrum of said molding comprising a band in the region of (3700-3750)+/−20 cm$^{-1}$ and a band in the region of (3670-3690)+/−20 cm$^{-1}$, wherein the intensity ratio of the band in the region of (3700-3750)+/−20 cm$^{-1}$ relative to the band in the region of (3670-3690)+/−20 cm$^{-}$is at most 1.5, preferably at most 1.4. These IR characteristics are understood as being determined according the Reference Example 3.6 of the present invention.

Preferably, during the normal run stage, the propylene oxide selectivity of the epoxidation reaction in the epoxidation reaction zone according to (ii) is at least 95%, preferably at least 96%, more preferably at least 97%, wherein the propylene oxide selectivity is defined as the molar amount of propylene oxide comprised in the effluent stream removed in (iii) relative to the molar amount of hydrogen peroxide comprised in the liquid feed stream provided in (i) at a given point of time during the normal run stage. If the epoxidation zone according to (ii) consists of the first epoxidation subzone, the propylene oxide selectivity is defined as the molar amount of propylene oxide comprised in the effluent stream removed from the one or more epoxidation reactors A in (iii) relative to the molar amount of hydrogen peroxide comprised in the liquid feed stream provided in (i) at a given point of time during the normal run stage. If the epoxidation zone according to (ii) consists of the first epoxidation subzone and the second epoxidation subzone arranged downstream of the first epoxidation subzone, the propylene oxide selectivity is defined as the molar amount of propylene oxide comprised in the effluent stream removed from the one or more epoxidation reactors B in (iii) relative to the molar amount of hydrogen peroxide comprised in the liquid feed stream provided in (i) at a given point of time during the normal run stage.

Start-Up Stage

Generally, the setup of the the start-up stage of the process of the present invention is not subject to any specific restrictions. Preferably, the start-up stage comprises
(a) continuously providing a liquid feed stream comprising propene, acetonitrile, and optionally propane and continuously passing said liquid feed stream under start-up conditions for a period of time $t_1$ into the epoxidation zone comprising the catalyst comprising a titanium zeolite having framework type MWW;
   wherein after the period of time $t_1$, the start-up stage further comprises
(b) continuously providing a liquid feed stream comprising hydrogen peroxide, admixing said liquid feed stream to the liquid feed stream provided in (a) obtaining a liquid feed stream comprising hydrogen peroxide, propene, acetonitrile, and optionally propane, and continuously passing said liquid feed stream under start-up conditions for a period of time $t_2$ into the epoxidation zone comprising the catalyst comprising a titanium zeolite having framework structure type MWW,
   wherein the liquid feed stream according to (b) comprises the formate salt, wherein the molar amount of the formate salt relative to the molar amount of hydrogen peroxide at a given point of time during step (b) of the start-up stage is $a^S(Fo/H_2O_2)$,
   wherein after the period of time $t_2$, the normal run stage begins and $a^S(Fo/H_2O_2)$ is $a^N(Fo/H_2O_2)$ at the beginning of the normal run stage, preferably being in the range of from $1.0*10^{-4}$ to $1.0*10^{-2}$, more preferably in the range of from $5*10^{-4}$ to $1.0*10^{-3}$.

Preferably at least 98 weight-%, more preferably at least 99 weight-%, more preferably from 99 to 100 weight-% of the liquid feed stream provided in (a) consist of propene, acetonitrile, and optionally propane. It is preferred that during the start-up stage, the composition of this stream is kept essentially constant, more preferably kept constant, and it is further preferred that the composition of this stream is not changed when the start-up stage ends and the normal run stage begins.

Preferably, the liquid feed stream according to (a) comprises hydrogen peroxide in an amount in the range of from 0 to 0.01 weight-%, preferably in the range of from 0 to 0.001 weight-%, more preferably in the range of from 0 to 0.0001 weight-%, based on the total weight of the liquid feed stream. Therefore, it is preferred that the liquid feed stream according to (a) is essentially free of hydrogen peroxide, more preferably free of hydrogen peroxide.

Preferably, the liquid feed stream according to (a) comprises the formate salt in an amount in the range of from 0 to 0.01 weight-%, preferably in the range of form 0 to 0.001 weight-%, more preferably in the range of from 0 to 0.0001 weight-%, based on the total weight of the liquid feed stream. Therefore, it is preferred that the liquid feed stream according to (a) is essentially free of the formate salt, more preferably free of the formate salt.

During the start-up stage, the start-up conditions comprise a start-up temperature $T^S$, wherein $T^S$ is the temperature of a heat transfer medium used for adjusting the temperature of the mixture in the epoxidation reaction zone, preferably by passing the heat transfer medium through a jacket of the epoxidation zone, wherein $T^S$ is preferably the temperature of the heat transfer medium prior to adjusting the temperature of the mixture, preferably the temperature of the heat transfer medium at the entrance of the jacket of the epoxidation zone.

At the beginning of the start-up stage, $T^S$ is preferably in the range of from 10 to 60° C., more preferably in the range of from 20 to 50° C., more preferably in the range of from 30 to 40° C.

During the start-up stage, the average rate of change of $T^S$ is preferably in the range of from −1 to 1 K*h$^{-1}$, more preferably in the range of from −0.5 to 0.5 K*h$^{-1}$, more preferably in the range of from −0.1 to 0.1 K*h$^{-1}$. The term "average rate of change of $T^S$" is defined as $[T^S(t_{max})-T^S(t_0)]/[t_{max}-t_0]$, wherein $[t_{max}-t_0]$ is the duration of the start-up stage defined by the difference from the end point of the start-up stage at a time $t_{max}$ and the start point of the start-up stage at a time $t_0$, wherein $T^S(t_{max})$ is the value of $T^S$ at the time $t_{max}$ and wherein $T^S(t_0)$ is the value of $T^S$ at the time $t_0$.

When the epoxidation zone comprises a first epoxidation subzone consisting of one or more epoxidation reactors A, wherein, if the first epoxidation subzone comprises two or more epoxidation reactors A, the two or more epoxidation reactors A are preferably arranged in parallel, and wherein the liquid feed stream provided is preferably passed into at least one of the epoxidation reactors A, it is preferred that $T^S$ is the temperature of a heat transfer medium used for adjusting the temperature of the mixture in the first epoxidation subzone, preferably by passing the heat transfer medium through a jacket of the first epoxidation subzone, wherein $T^S$ is preferably the temperature of the heat transfer medium prior to adjusting the temperature of the mixture, preferably the temperature of the heat transfer medium at the entrance of the jacket of the first epoxidation subzone.

Preferably, the liquid stream according to (b) comprises hydrogen peroxide and is admixed to the liquid feed stream provided in (a) is an aqueous hydrogen peroxide stream. Preferably, said aqueous hydrogen peroxide stream has a hydrogen peroxide concentration in the range of from 25 to 75 weight-%, more preferably in the range of from 30 to 50 weight-%, based on the total weight of the aqueous hydrogen peroxide stream.

Preferably, said aqueous hydrogen peroxide stream comprises sodium Na$^+$ at a molar ratio of sodium relative to hydrogen peroxide in the range of from $1*10^{-6}$:1 to $250*10^{-6}$, more preferably from $5*10^{-6}$:1 to $50*10^{-6}$:1.

Preferably, during the start-up stage, the liquid feed stream passed in to the epoxidation zone contains ammonium $NH_4^+$ in an amount in the range of from 0 to 2 weight-ppm, preferably in the range of from 0 to 1 weight-ppm, based on the total weight of the liquid feed stream.

Generally, it is conceivable that the start-up stage comprises, in addition to (a) and (b), one or more further steps. Preferably, the start-up stage consists of (a) and (b).

Preferably, during the start-up stage, the average rate of change of $a^S(Fo/H_2O_2)$ is greater than 0. The term "average rate of change of $a^S(Fo/H_2O_2)$" as used in the context of the present invention is defined as $[a^S(Fo/H_2O_2)(t_{max})-a^S(Fo/H_2O_2)(t_0)]/[t_{max}-t_0]$, wherein $[t_{max}-t_0]$ is the duration of the start-up stage defined by difference from the end point of the start-up stage at a time $t_{max}$ and the start point of the start-up stage at a time $t_0$, wherein $a^S(Fo/H_2O_2)(t_{max})$ is the value of $a^S(Fo/H_2O_2)$ at the time $t_{max}$ and wherein $a^S(Fo/H_2O_2)(t_0)$ is the value of $a^S(Fo/H_2O_2)$ at the time $t_0$.

According to a first preferred embodiment, the average rate of change of $a^S(Fo/H_2O_2)$ during step (b) of the start-up stage is in the range of from $1*10^{-5}$ to $1*10^{-3}$ h$^{-1}$, preferably in the range of from $5*10^{-5}$ to $1*10^{-4}$ h$^{-1}$. According to this embodiment, it is preferred that the starting concentration of the formate salt in (b) is the pre-determined concentration of the formate salt to be present at the beginning of the normal run stage. In this case, it is further preferred that the starting concentration of the hydrogen peroxide in (b) is in the range of from 0.1 to 50%, more preferably in the range of from 0.5 to 20%, more preferably in the range of from 1 to 10% of the pre-determined concentration of the hydrogen peroxide to be present at the beginning of the normal run stage.

According to a second preferred embodiment, the average rate of change of $a^S(Fo/H_2O_2)$ during step (b) of the start-up stage is in the range of from $1*10^{-6}$ to $5*10^{-5}$ h$^{-1}$, preferably in the range of from $5*10^{-6}$ to $1*10^{-5}$ h$^{-1}$. According to this embodiment, it is preferred that at the beginning of (b), the concentration of the formate salt is in the range of from 2 to 50%, more preferably in the range of from 5 to 40%, more preferably in the range of from 10 to 34% of the pre-determined concentration of the formate salt to be present at the beginning of the normal run stage. It is further preferred that according to this embodiment and during (b), the hydrogen peroxide concentration is increased, preferably stepwise increased, until the pre-determined concentration of the hydrogen peroxide to be present at the beginning of the normal run stage is reached. Further preferably according to this embodiment, the concentration of the formate salt is then increased, for example stepwise increased, until the pre-determined concentration of the formate salt to be present at the beginning of the normal run stage.

Generally, it is preferred that during the start-up stage, preferably during step (b) of the start-up stage, $a^S(Fo/H_2O_2)$ is changed stepwise.

Preferably, during the start-up stage, the maximum temperature of the liquid mixture in the epoxidation zone is in the range of from 70 to 100° C., such as in the range of from 70 to 90° C. or in the range of from 70 to 80° C.

As mentioned above, the process of the present invention is characterized in an especially long lifetime of the epoxidation catalyst used and, thus, in especially long normal run stages. Preferably, the normal run stage lasts for at least 5,000 h, preferably at least 10,000 h, more preferably at least 15,000 h.

As also mentioned above, the process of the present invention allows for superior selectivities with regard to the valuable product propylene oxide, in particular until the end of the normal run stage, even in cases where during the normal run stage, the epoxidation temperature is slightly increased or generally increased for achieving a constant and very high hydrogen peroxide conversion. Therefore, the present invention also relates to a method for increasing the propylene oxide selectivity of a catalyst comprising a titanium zeolite having framework type MWW in a continuous process for preparing propylene oxide, said continuous process for preparing propylene oxide comprising (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time is $a^N(Fo/H_2O_2)$;

(ii) continuously passing the liquid feed stream provided in (i) into an epoxidation zone comprising the catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;

said method for increasing the propylene oxide selectivity comprising decreasing $a^N(Fo/H_2O_2)$ in the course of said continuous process at otherwise constant epoxidation conditions. Preferably, the formate salt is a potassium formate salt and the titanium zeolite having framework type MWW comprised in the catalyst according to (ii) contains titanium, calculated as elemental titanium, in an amount in the range of from 0.1 to 5 weight-%, preferably in the range of from 1 to 2 weight-%, based on the total weight of the titanium zeolite having framework type MWW and contains zinc, calculated as elemental zinc, in an amount in the range of from 0.1 to 5 weight-%, preferably in the range of from 1 to 2 weight-%, based on the based on the total weight of the titanium zeolite having framework type MWW.

Further Downstream Stages

The effluent stream removed according to (iii) may contain at least one component B wherein the normal boiling point of the at least one component B is higher than the normal boiling point of acetonitrile and wherein the decadic logarithm of the octanol-water partition coefficient (log $K_{OW}$) of the at least one component B is greater than zero. Regarding the determination of the octanol-water partition coefficient, reference is made to Reference Example 4 hereinbelow. Typically, the at least one component B contained in the effluent stream removed according to (iii) either is a by-product and/or a side-product obtained during the epoxidation reaction in (ii), and/or is a compound which is formed during at least one of the work-up stages being preferably carried out downstream of step (ii) and which accumulates if certain process streams of the preferred integrated process are recycled into (i), and/or is contained as an impurity in at least one of the starting materials employed in (i) such as an impurity in the acetonitrile or an impurity in the hydrogen peroxide. Preferably, the at least one component B is propionitrile, 1-nitropropane, 2-nitropropane, 3-methylbutanenitrile, n-pentanenitrile, 1-pentanol, 2-pentanol, 2-butanone, 2-pentanone, 2-hexanone, 4-methyl-2-heptanone, 2,6-dimethyl-4-heptanol, 4,6-dimethyl-2-heptanol,2,6-dimethyl-4-heptanone, 4,6-dimethyl-2-heptanone, 2,6-dimethyl-4,6-heptandiol, 2,4-dimethyloxazoline, 2,5-dimethyloxazo-line, cis-2,4-dimethyl-1,3-dioxolane, trans-2,4-dimethyl-1,3-dioxolane, at least one impurity contained in the hydrogen peroxide stream employed in (i), or a combination of two or more of these compounds. Preferably, the at least one impurity contained in the hydrogen peroxide stream employed in (i) is an alkyl phosphate such as tris-(2-ethylhexyl) phosphate, a nonyl alcohol such as diisobutylcarbinol, an alkylcyclohexanol ester such as 2-methyl-cyclohexylacetate, an N,N-dialkyl carbonamide such as N,N-dibutylpropionamide, an N-alkyl-N-aryl carbonamide such as N-ethyl-N-phenylbenzamide, an N,N-dialkyl carbamate such as 2-ethylhexyl-N-butylcarbamate, a tetraalkyl urea such as tetra-n-butylurea, a cyclic urea derivative such as 1,3-dihexyltetrahydro-2(1H)-pyrimidone, a phenylalkyl urea such as N,N-dibutyl-N'-methyl-N'-phenylurea, an N-alkyl-2-pyrrolidone such as octyl pyrrolidone, an N-alkyl caprolactam such as n-octyl caprolactam, or a combination of two or more of these compounds.

From the effluent stream removed according to (iii), propylene oxide can be separated according to any conceivable method. Preferably, the effluent stream removed in (iii) comprises propene and optionally propane, and the process of the present invention, in addition to steps (i), (ii), and (iii), further comprises (iv) separating propene, optionally together with propane, and oxygen which is optionally additionally contained in the effluent stream, from the effluent stream, obtaining a stream S01 enriched in propylene oxide, acetonitrile, and water, wherein preferably at least 99 weight-% of S01 consist of acetonitrile, water, and propylene oxide; wherein for separation, preferably a fractionation unit is used, wherein preferably, at the top of the fractionation unit, liquid acetonitrile, optionally admixed with liquid water, is added as entraining agent, and wherein S01 is preferably obtained as bottoms streams;

(v) separating propylene oxide from S01, obtaining a top stream comprising propylene oxide and being depleted of acetonitrile and water.

Preferably, prior to (iv), the effluent stream is subjected to a suitable pressure release stage and passed to the separation stage according to (iv). Optionally, the possibly formed gaseous and liquid phases are suitably separated and passed to different trays of the distillation tower employed according to (iv) if the separation according to (iv) is carried via distillation. Alternatively, the effluent stream can be subjected to said pressure release directly in the distillation column employed according to (iv); in this case, no pressure release apparatus downstream of the epoxidation stage and upstream of the separation stage according to (iv) would be necessary. Optionally, the temperature of the effluent stream can be suitably adjusted prior to (iv), preferably after the pressure release stage.

Preferably, in (v), a further stream S02 is obtained, preferably as bottoms stream, which is enriched in acetonitrile and water. Preferably, at least 95 weight-% of S02 consist of acetonitrile and water, wherein more preferably, the weight ratio of acetonitrile relative to water in the stream S02 is greater than 1:1. Therefore, the present invention relates to the process as described above, which comprises (v) separating propylene oxide from S01, obtaining a top stream comprising propylene oxide and being depleted of acetonitrile and water, and obtaining a stream S02, preferably as bottoms stream, enriched in acetonitrile and water, wherein at least 95 weight-% of S02 consist of acetonitrile and water, and wherein the weight ratio of acetonitrile relative to water is greater than 1:1.

Further, the present invention relates to a process comprising (iv) separating propene, optionally together with propane, and oxygen which is optionally additionally contained in the effluent stream, from the effluent stream, obtaining a stream S01 enriched in propylene oxide, acetonitrile, water, and optionally the at least one component B, wherein preferably at least 99 weight-% of S01 consist of acetonitrile, water, preferably the at least one component B, and propylene oxide; wherein for separation, preferably a fractionation unit is used, wherein preferably, at the top of the fractionation unit, liquid acetonitrile, optionally admixed with liquid water, is added as entraining agent, and wherein S01 is preferably obtained as bottoms streams;

(v) separating propylene oxide from S01, obtaining a top stream comprising propylene oxide and being depleted of acetonitrile and water, and obtaining a stream S02, preferably as bottoms stream, enriched in acetonitrile, water and optionally the at least one component B, wherein preferably at least 95 weight-% of S02 consist of acetonitrile, water and preferably the at least one component B, and wherein the weight ratio of acetonitrile relative to water is greater than 1.1.

Regarding step (iv), no specific restrictions exist. Preferably, the separation is carried out so that at least 90 weight-%, more preferably at least 95 weight-%, more preferably at least 98 weight-%, more preferably at least 99 weight-% of S01 consist of acetonitrile, water, preferably the at least one component B, and propylene oxide. Preferably, a fractionation unit is employed for the separation in (iv). Further preferably, the separation in (iv) is carried out in at least one distillation tower, more preferably in one distillation tower. From this distillation tower, S01 is preferably obtained as bottoms stream. Preferably, this distillation tower has from 10 to 30, more preferably from 15 to 25 theoretical trays. The distillation tower is preferably operated at a top pressure of from 0.5 to 1.2 bar, more preferably of from 0.7 to 1.1 bar. In order to facilitate said separation task, it was found that it is advantageous to add either liquid acetonitrile or a liquid mixture of acetonitrile with water to the top of the column. It is believed that this external reflux serves as entraining agent which, among others, prevents propylene oxide from being separated via the top of the distillation tower. According to a preferred embodiment of the present invention, a portion of the bottom stream of the distillation tower preferably employed in stage (v) is used. It is also conceivable that the stream TL2 described hereinbelow or a portion thereof is used as entraining agent. The amount of TL2 will not be sufficient, and another stream is to be added. Preferably, the weight ratio of the amount of acetonitrile fed as external reflux to the top of the distillation tower relative to the weight of the effluent stream removed in (iii) fed into the distillation tower and to be separated in the distillation tower is in the range of from 1:1 to 4:1 preferably from 1.5:1 to 3:1. The temperature of the external reflux is generally in the range of from 2 to 20° C., preferably in the range of from 5 to 15° C. According to the present invention, preferably at least 85 volume-%, more preferably at least 90 volume-%, more preferably at least 93 volume-% of the top stream of the distillation column according to (iv) consist of propene, oxygen, and optionally propane. Depending on its oxygen content, this top stream can be passed to a further suitable work-up stage wherein the oxygen content is suitably decreased in order to allow, e.g., for recycling the oxygen-depleted stream to be recycled to one or more stages of the present invention, such as a starting material for step (ii) of the inventive process like stage (ii-1) or stage (ii-3), or as portion of the stream P described hereinbelow. If the oxygen content of said top stream is reduced, it is preferred to reduce the oxygen by reaction with hydrogen in the presence of a suitable catalyst. For example, it is possible to use catalysts comprising copper in elemental and/or oxidic form on a support, wherein copper is present on the support in an amount of 30 to 80 weight-% based on the whole catalyst and calculated as CuO. Such catalysts can be prepared, for example, according to the example of EP 0 427 062 A2, catalyst 2, page 4, lines 41 to 50 (corresponding to U.S. Pat. No. 5,194,675). In order to reduce the oxygen content, also other suitable methods are conceivable. Optionally, said top stream, prior to be subjected to hydrogenation, can be compressed and partially condensed wherein a liquid stream is obtained which essentially consists of propene and optionally propane and acetonitrile and which contains minor amounts of water. The non-condensed portion essentially consists of propene and optionally propane and oxygen and contains a minor amount of water wherein, compared to the basic stream, the oxygen content is increased while still being in a range so that the mixture is not ignitable. This oxygen-enriched stream is then subjected to hydrogenation.

Regarding step (v), no specific restrictions exist. Preferably, the separation is carried out so that preferably at least 90 weight-%, more preferably at least 95 weight-%, more preferably at least 99 weight-% of S02 consist of acetonitrile, water and optionally the at least one component B. More preferably, the weight ratio of acetonitrile relative to water in S02 is greater than 1:1, preferably in the range of from 2:1 to 10:1, more preferably from 2.5:1 to 5:1. Preferably, a fractionation unit is employed for the separation in (v). Further preferably, the separation in (v) is carried out in at least one distillation tower, more preferably in one distillation tower. Preferably, this tower has of from 50 to 80, more preferably of from 60 to 70 theoretical trays. The distillation tower is preferably operated at a top pressure of from 0.2 to 2 bar, more preferably of from 0.4 to 1 bar. Optionally, at least one suitable polar solvent or a mixture of two or more polar solvents, preferably water, can be added in the upper part of the column as extracting agent.

According to an embodiment of the process of the present invention, the separation according to step (v) can be carried out by introducing S01 into an extractive distillation column;

additionally introducing a polar extracting solvent or a mixture of two or more thereof, preferably water, into said extractive distillation column;

distilling propylene oxide overhead from said extractive distillation column as top stream, wherein the top stream comprises only minor amounts of acetonitrile such as 500 ppm or less;

compressing said top stream obtained overhead in the previous step by means of at least one compressor to give a compressed vapor;

condensing the compressed vapor obtained in the previous step and returning at least part of the heat of condensation to at least one reboiler employed in the extractive distillation column.

From this distillation tower according to (v), a top stream is obtained which contains preferably at least 90 weight-%, more preferably at least 95 weight-%, more preferably at least 99 weight-% of propylene oxide. Further from this distillation tower, S02 is preferably obtained as bottoms stream which preferably contains 500 weight-ppm at most, preferably 100 weight-ppm at most, and more preferably 60 weight-ppm at most of propylene oxide, based on the weight of S02. Depending on the requirements on the propylene oxide quality, it is conceivable to use this propylene oxide fraction without any further purification. It is, however, also conceivable to further purify said propylene oxide fraction, for example in at least one further distillation stage.

From the distillation tower according to (v) or optionally from the further distillation stage, a propylene oxide stream is obtained wherein preferably at least 99.990 weight-%, more preferably at least 99.995 weight-%, more preferably at least 99.999 weight-% of said stream consist of propylene oxide.

Therefore, the present invention also relates to a composition comprising at least 99.990 weight-%, preferably at least 99.995 weight-%, more preferably at least 99.999 weight-% of propylene oxide, preferably obtainable or obtained by a process comprising steps (iv) and (v) as described above.

Generally, the stream S02 as described above can be used as acetonitrile recycle stream which can be used for providing the liquid feed stream in (i). Further, it is possible that the stream S02 is subjected to further work-up steps before it is used as acetonitrile recycle stream which is used for providing the liquid feed stream in (i). Preferably, the stream S02 is subjected to the further work-up steps described hereinbelow in the embodiments 1 to 13.

Prior to Step (vi) as Described Below, it is Conceivable
(v-01) to subject the stream S02 obtained from step (v) to hydrogenation; and/or
(v-02) to subject the stream obtained from (v) or from (v-01) to distillation to obtain a bottoms stream,
wherein the hydrogenated stream obtained from (v-01) or the bottoms stream obtained from (v-02) is subjected to further work-up as stream S1. If steps (v-01) and/or (v-02) is/are carried out, it is preferred
(v-01) to subject the stream S02 obtained from (v) to a catalytical hydrogenation stage, the catalyst preferably being a heterogeneous catalysts comprising Ru, Ni, Pd, Pt, either individually or as a mixture of two or more thereof, as active metal on a suitable support material, in particular Pd on activated carbon; said hydrogenation preferably being carried out at a pressure during hydrogenation in the range of from 1 to 100 bar(abs), preferably from 1 to 10 bar(abs), and a temperature during hydrogenation in the range of from 0 to 180° C., preferably from 25 to 120° C., more preferably from 65 to 85° C.; and/or
(v-02) to subject the stream obtained from (v) or from (v-01) to a distillation stage, preferably carried out in a distillation column operated at a top pressure of from 0.7 to 2 bar, more preferably of from 1.1 to 2 bar.

Preferably, the process of the present invention neither comprises (v-01) nor (v-02).

Further Work-up Steps

Preferably, in particular if the liquid feed stream provided in (i) comprises the at least one component B, the further work-up stages are carried out by a process whose preferred steps and conditions are defined by the following embodiments 1 to 13 and the respective combinations of embodiments resulting from the dependencies as indicated:

1. (vi) dividing S1 into two streams S2 and S3, wherein the total weight of S3 relative to the total weight of S1 is in the range of from 0.01 to 25%;
   (vii) subjecting S3 to a vapor-liquid fractionation in a fractionation unit, obtaining a vapor fraction stream S4 being depleted of the at least one component B, and obtaining a liquid bottoms stream S4b being depleted of acetonitrile;
   (viii) recycling at least a portion of S4, optionally after work-up, to (i).
2. The process of embodiment 1, wherein in (vi), the total weight of S3 relative to the total weight of S1 is in the range of from 0.05 to 20%, preferably from 0.1 to 15%, more preferably from 0.2 to 10%, more preferably from 0.5 to 5%.
3. The process of embodiment 1 or 2, wherein from 90 to 99.9 weight-%, preferably from 95 to 99.8 weight-%, more preferably from 99 to 99.7 weight-% of S1 consist of acetonitrile and water and wherein preferably from 0.01 to 5 weight-%, more preferably from 0.015 to 3 weight-%, more preferably from 0.02 to 2 weight-% of S1 consist of the at least one component B.
4. The process of any of embodiments 1 to 3, wherein in (vii), vapor-liquid fractionation is carried out in the fractionation unit so that from 10 to 30 weight-%, preferably from 10 to 25 weight-% of the liquid bottoms stream S4b consist of acetonitrile and from 0.1 to 10 weight-%, preferably from 0.25 to 5 weight-% of the liquid bottoms stream S4b consist of the at least one further component B.
5. The process of any of embodiments 1 to 4, wherein in (vii), vapor-liquid fractionation is carried out in the fractionation unit at an absolute pressure in the range of from 0.1 to 10 bar, preferably from 0.5 to 5 bar, more preferably from 1 to 2 bar.
6. The process of any of embodiments 1 to 5, wherein in (vii), the number of theoretical trays of the fractionation unit is in the range of from 1 to 100, preferably from 2 to 25, more preferably from 3 to 10.
7. The process of any of embodiments 1 to 6, wherein a fraction of S4 is used after condensation as reflux, the reflux ratio preferably being in the range of from 0.01:1 to 10:1, more preferably from 0.1:1 to 5:1, more preferably from 0.5:1 to 2:1.
8. The process of any of embodiments 1 to 6, wherein the fractionation unit is operated without reflux and S3 is fed to the top of the fractionation unit.
9. The process of any of embodiments 1 to 8, wherein from 95 to 99.99 weight-%, preferably from 97 to 99.9 weight-%, more preferably from 98 to 99.9 weight-% of S4 consist of acetonitrile and water, and wherein preferably from 0.0001 to 0.2 weight-%, more preferably from 0.001 to 0.15 weight-%, more preferably from 0.005 to 0.1 weight-% of S4 consist of the at least one component B.
10. The process of any of embodiments 1 to 9, wherein (viii) comprises recycling at least a portion of S4, optionally after work-up, to (i), and recycling at least a portion of S2, optionally after work-up, to step (i).

According to the present invention, the effluent stream removed according to (iii) comprises at least a portion of the formate salt comprised in the feed stream provided in (i). Preferably, the propylene oxide is separated from the effluent stream in one or more suitable stages described hereinabove. Further preferably, the thus obtained stream depleted of propylene oxide is subjected to one or more further stages from which an acetonitrile recycle stream is preferably obtained which is fed back to the epoxidation reaction. A preferred recycling method comprising a stage (viii) is described hereinabove. Preferably, at least a portion of the at least one formate salt comprised in the effluent stream according to (iii) and preferably comprised in the stream S4, more preferably in the streams S4 and S2, is suitably separated from the recycle stream(s) during work-up of S2 and/or S4. More preferably, at least 99%, preferably at least 99.9%, more preferably at least 99.99% of the at least one formate salt comprised in S4, preferably comprised in the streams S4 and S2, are separated from the recycle stream(s) during work-up of S2 and/or S4. Therefore, it is especially preferred that an accumulation of the at least one formate salt caused by a re-use of the recycle stream(s) in (i) is essentially completely prevented.

The present invention is further illustrated by the following embodiments and combinations of embodiments as indicated by the respective dependencies and back-references.

1. A continuous process for preparing propylene oxide comprising a start-up stage and a normal run stage, wherein the normal run stage comprises
    (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$;
    (ii) continuously passing the liquid feed stream provided in (i) into an epoxidation zone comprising a catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;
    (iii) continuously removing an effluent stream from the epoxidation zone, the effluent stream comprising propylene oxide, acetonitrile, water, at least a portion of the formate salt, optionally propene, and optionally propane;
    wherein the normal run stage is characterized in an average rate of change of $a^N(Fo/H_2O_2)$ of less than 0 $h^{-1}$.
2. The continuous process of embodiment 1, wherein the average rate of change of $a^N(Fo/H_2O_2)$ is in the range of from $-10^{-10}$ to $-10^{-6}$ $h^{-1}$.
3. The continuous process of embodiment 1 or 2, wherein the average rate of change of $a^N(Fo/H_2O_2)$ is in the range of from $-10^{-9}$ to $-10^{-7}$ $h^{-1}$.
4. The continuous process of any one of embodiments 1 to 3, wherein at the beginning of the normal run stage, $a^N(Fo/H_2O_2)$ is in the range of from $1.0*10^{-4}$ to $1.0*10^{-2}$.
5. The continuous process of any one of embodiments 1 to 4, wherein at the beginning of the normal run stage, $a^N(Fo/H_2O_2)$ is in the range of from $5*10^{-4}$ to $1.0*10^{-3}$.
6. The continuous process of any one of embodiments 1 to 5, wherein the epoxidation zone according to (ii) comprises a first epoxidation subzone consisting of one or more epoxidation reactors A, wherein, if the first epoxidation subzone comprises two or more epoxidation reactors A, the two or more epoxidation reactors A are arranged in parallel, and wherein in (ii), the liquid feed stream provided in (i) is passed into at least one of the epoxidation reactors A.
7. The continuous process of embodiment 6, wherein the epoxidation zone according to (ii) consists the first epoxidation subzone.
8. The continuous process of embodiment 6 or 7, wherein during the normal run stage, the epoxidation conditions according to (ii) comprise an epoxidation temperature $T^N$ and wherein during the normal run stage, the average rate of change of $T^N$ is in the range of from 0 to 50 $K*h^{-1}$, wherein $T^N$ is the temperature of a heat transfer medium used for adjusting the temperature of the reaction mixture in the first epoxidation reaction subzone according to (ii), preferably by passing the heat transfer medium through a jacket of the one or more epoxidation reactors A, wherein $T^N$ is preferably the temperature of the heat transfer medium prior to adjusting the temperature of the reaction mixture, preferably the temperature of the heat transfer medium at the entrance of the jacket of the one or more epoxidation reactors A.
9. The continuous process of embodiment 8, wherein the average rate of change of $T^N$ is in the range of from 0 to 40 $K*h^{-1}$, preferably in the range of from 0 to 30 $K*h^{-1}$, more preferably in the range of from 0 to 30 $K*h^{-1}$.
10. The continuous process of embodiment 8 or 9, wherein during the initial stage of the normal run stage, the average rate of change of $T^N$ is in the range of from 0 to 0.5 $K*h^{-1}$, preferably in the range of from 0 to 0.2 $K*h^{-1}$, more preferably in the range of from 0 to 0.1 $K*h^{-1}$, and wherein, after said initial stage, when $a^N(Fo/H_2O_2)$ is in the range of from 40 to 60%, preferably 45 to 55% of $a^N(Fo/H_2O_2)$ at the beginning of the normal stage, $T^N$ is increased by at least 0.1° C., preferably by at least 0.5° C., preferably by at least 1° C.
11. The continuous process of any one of embodiments 8 to 10, wherein during the normal run stage, $T^N$ is in the range of from 20 to 70° C., preferably in the range of from 25 to 65° C., more preferably in the range of from 30 to 60° C.
12. The continuous process of any one of embodiments 6 to 11, wherein during the normal run stage, the epoxidation conditions according to (ii) comprise a first epoxidation reaction pressure in the range of from 14 to 100 bar, preferably in the range of from 15 to 32 bar, more preferably in the range of from 15 to 25 bar, wherein the first epoxidation reaction pressure is defined as the absolute pressure at the exit of the first epoxidation subzone.
13. The continuous process of any one of embodiments 6 to 12, wherein during the normal run stage, the epoxidation conditions according to (ii) comprise a catalyst loading in the first epoxidation subzone in the range of from 0.05 to 1.25 $h^{-1}$, preferably in the range of from 0.1 to 1 $h^{-1}$, more preferably in the range of from 0.2 to 0.7 $h^{-1}$, wherein the catalyst loading is defined as the ratio of the mass flow rate in kg/h of hydrogen peroxide contained in liquid feed stream provided in (i) relative to the amount in kg of catalyst comprising a titanium zeolite having framework type MWW comprised in the first epoxidation subzone according to (ii).
14. The continuous process of any one of embodiments 6 to 13, wherein the epoxidation zone additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone.
15. The continuous process of embodiment 14, wherein the epoxidation zone according to (ii) consists of the first epoxidation subzone and the second epoxidation subzone.
16. The continuous process of embodiment 14 or 15, wherein during the normal run stage, the epoxidation conditions according to (ii) comprise a second epoxidation reaction pressure in the range of from 14 to 100 bar, preferably in the range of from 14.5 to 32 bar, more preferably in the range of from 15 to 25 bar, wherein the second epoxidation reaction pressure is defined as the absolute pressure at the exit of the second epoxidation subzone.

17. The continuous process of any one of embodiments 14 to 16, wherein during the normal run stage, the epoxidation conditions according to (ii) comprise a catalyst loading in the second epoxidation subzone in the range of from 0.001 to 0.5 h$^{-1}$, preferably in the range of from 0.005 to 0.3 h$^{-1}$, more preferably in the range of from 0.01 to 0.2 h$^{-1}$, wherein the catalyst loading is defined as the ratio of the mass flow rate in kg/h of of hydrogen peroxide contained in the feed stream passed into the second epoxidation subzone relative to the amount in kg of catalyst comprising a titanium zeolite having framework type MWW comprised in the second epoxidation subzone according to (ii).

18. The continuous process of any one of embodiments 14 to 17, wherein the temperature of the reaction mixture in the second epoxidation reaction subzone is not adjusted by passing a heat transfer medium through a jacket of the one or more epoxidation reactors B, wherein preferably, the second epoxidation subzone is an essentially adiabatic epoxidation subzone, more preferably an adiabatic epoxidation subzone.

19. The continuous process of any one of embodiments 1 to 18, wherein during the normal run stage, the epoxidation conditions according to (ii) comprise a hydrogen peroxide conversion $c^N(H_2O_2)$, wherein the average rate of change of $c^N(H_2O_2)$ is in the range of from $-1.0*10^{-3}$ to $1.0*10^{-3}$%-points*h$^{-1}$, wherein $c^N(H_2O_2)$ is defined as the molar amount of hydrogen peroxide comprised in the effluent stream removed in (iii) relative to the molar amount of hydrogen peroxide comprised in the liquid feed stream provided in (i) at a given point of time during the normal run stage, wherein during the normal run stage, $c^N(H_2O_2)$ is preferably in the range of from 80 to 100%, more preferably from 90 to 100%, more preferably from 95 to 100%, more preferably from 99 to 100%, more preferably from 99.5 to 100%.

20. The continuous process of any one of embodiments 1 to 19, wherein the formate salt according to (i) comprises, preferably consists of, a potassium formate salt, preferably K$^+$COO$^-$.

21. The continuous process of any one of embodiments 1 to 20, wherein in the epoxidation zone according to (ii), the reaction mixture is liquid under the epoxidation conditions.

22. The continuous process of embodiment 21, wherein in the epoxidation zone according to (ii), the reaction mixture consists of one single liquid phase under the epoxidation conditions.

23. The continuous process of any one of embodiments 1 to 22, wherein according to (ii), the catalyst comprising a titanium zeolite having framework type MWW is present in the epoxidation zone as a fixed-bed catalyst.

24. The continuous process of any one of embodiments 1 to 23, wherein the titanium zeolite having framework type MWW comprised in the catalyst according to (ii) contains titanium, calculated as elemental titanium, in an amount in the range of from 0.1 to 5 weight-%, preferably in the range of from 1 to 2 weight-%, based on the total weight of the titanium zeolite having framework type MWW.

25. The continuous process of any one of embodiments 1 to 247, wherein the titanium zeolite having framework type MWW comprised in the catalyst according to (ii) contains zinc, calculated as elemental zinc, in an amount in the range of from 0.1 to 5 weight-%, preferably in the range of from 1 to 2 weight-%, based on the total weight of the titanium zeolite having framework type MWW.

26. The continuous process of any one of embodiments 1 to 25, wherein the catalyst comprising the titanium zeolite having framework type MWW is in the form of a molding, comprising the titanium zeolite having framework type MWW and a binder, preferably a silica binder, wherein the catalyst comprises the titanium zeolite having framework type MWW preferably in an amount in the range of from 70 to 80 weight-%, based on the total weight of the catalyst, and the silica binder preferably in an amount of from 30 to 20 weight-%, based on the total weight of the catalyst, wherein preferably at least 99 weight-% of the catalyst consist of the titanium zeolite having framework type MWW together and the binder.

27. The continuous process of any one of embodiments 1 to 26, wherein during the normal run stage, the propylene oxide selectivity of the epoxidation reaction in the epoxidation reaction zone according to (ii) is at least 95%, preferably at least 96%, more preferably at least 97%, wherein the propylene oxide selectivity is defined as the molar amount of propylene oxide comprised in the effluent stream removed in (iii) relative to the molar amount of hydrogen peroxide comprised in the liquid feed stream provided in (i) at a given point of time during the normal run stage.

28. The continuous process of any one of embodiments 1 to 27, wherein during the normal run stage, the liquid feed stream provided in (i) comprises the acetonitrile in an amount in the range of from 60 to 75 weight-%, preferably in the range of from 60 to 65 weight-%, based on the total weight of the liquid feed stream; the hydrogen peroxide in an amount in the range of from 6 to 10 weight-%, preferably in the range of from 7 to 9 weight-%, based on the total weight of the liquid feed stream; the water at a molar ratio of water relative to acetonitrile of at most 1:4, preferably in the range of from 1:50 to 1:4, more preferably in the range of from 1:15 to 1:4.1, more preferably in the range of from 1:10 to 1:4.2;
the propene at a molar ratio of propene relative to hydrogen peroxide comprised in the liquid feed stream in the range of from 1:1 to 1.6:1, preferably in the range of from 1.1:1 to 1.5:1; and
optionally the propane at a molar ratio of propane relative to the sum of propene and propane in the range of from 0.0001:1 to 0.15:1, preferably in the range of from 0.001:1 to 0.05:1; wherein at least 95 weight-%, preferably from 95 to 100 weight-%, more preferably from 98 to 100 weight-% of the liquid feed stream provided in (i) consist of propene, hydrogen peroxide, acetonitrile, the formate salt, water and optionally propane.

29. The continuous process of any one of embodiments 1 to 28, wherein during the normal run stage, the liquid feed stream provided in (i) contains ammonium NH$_4^+$ in an amount in the range of from 0 to 2 weight-ppm, preferably in the range of from 0 to 1 weight-ppm, based on the total weight of the liquid feed stream.

30. The continuous process of any one of embodiment 1 to 29, wherein during the normal run stage, the liquid feed stream provided in (i) contains sodium Na$^+$ at a molar ratio of sodium relative to hydrogen peroxide in the range of from $1*10^{-6}$:1 to $250*10^{-6}$:1, preferably in the range of from $5*10^{-6}$:1 to $50*10^{-6}$:1.

31. The continuous process of any one of embodiments 1 to 30, wherein during the normal run stage, the liquid feed stream is provided in (i) by combining a stream comprising hydrogen peroxide, a stream comprising acetonitrile and optionally water, and a stream comprising propene and optionally propane, wherein an aqueous stream comprising the formate salt is combined with the stream comprising hydrogen peroxide, or with the stream comprising acetonitrile and optionally water, or with the stream comprising propene and optionally propane, or with a mixed stream of two or three of these streams, preferably with the stream comprising hydrogen peroxide, or with the stream comprising acetonitrile and optionally water, or with a mixed stream thereof.

32. The continuous process of embodiment 31, wherein the stream comprising hydrogen peroxide is an aqueous hydrogen peroxide stream having a hydrogen peroxide concentration in the range of from 25 to 75 weight-%, preferably from 30 to 50 weight-%, based on the total weight of the aqueous hydrogen peroxide stream.

33. The continuous process of embodiment 32, wherein the aqueous hydrogen peroxide stream comprises sodium at a molar ratio of sodium relative to hydrogen peroxide in the range of from $1*10^{-6}$:1 to $250*10^{-6}$, preferably from $5*10^{-6}$:1 to $50*10^{-6}$:1.

34. The continuous process of any one of embodiments 1 to 33, comprising a start-up stage prior to, preferably immediately prior to, the normal run stage, wherein the start-up stage comprises
    (a) continuously providing a liquid feed stream comprising propene, acetonitrile, and optionally propane and continuously passing said liquid feed stream under start-up conditions for a period of time $t_1$ into the epoxidation zone comprising the catalyst comprising a titanium zeolite having framework type MWW;
    wherein after the period of time $t_1$, the start-up stage further comprises
    (b) continuously providing a liquid feed stream comprising hydrogen peroxide, admixing said liquid feed stream to the liquid feed stream provided in (a) obtaining a liquid feed stream comprising hydrogen peroxide, propene, acetonitrile, and optionally propane, and continuously passing said liquid feed stream under start-up conditions for a period of time $t_2$ into the epoxidation zone comprising the catalyst comprising a titanium zeolite having framework structure type MWW,
    wherein the liquid feed stream according to (b) comprises the formate salt, wherein the molar amount of the formate salt relative to the molar amount of hydrogen peroxide at a given point of time during step (b) of the start-up stage is $a^S(Fo/H_2O_2)$,
    wherein after the period of time $t_2$, the normal run stage begins and $a^S(Fo/H_2O_2)$ is $a^N(Fo/H_2O_2)$ at the beginning of the normal run stage, preferably as defined in embodiment 4 or 5.

35. The continuous process of embodiment 34, wherein at least 98 weight-%, preferably at least 99 weight-%, more preferably from 99 to 100 weight-% of the liquid feed stream provided in (a) consist of propene, acetonitrile, and optionally propane.

36. The continuous process of embodiment 34 or 35, wherein the liquid feed stream according to (a) comprises hydrogen peroxide in an amount in the range of from 0 to 0.01 weight-%, preferably in the range of from 0 to 0.001 weight-%, more preferably in the range of from 0 to 0.0001 weight-%, based on the total weight of the liquid feed stream.

37. The continuous process of any one of embodiments 34 to 36, wherein the liquid feed stream according to (a) comprises the formate salt in an amount in the range of from 0 to 0.01 weight-%, preferably in the range of form 0 to 0.001 weight-%, more preferably in the range of from 0 to 0.0001 weight-%, based on the total weight of the liquid feed stream.

38. The continuous process of any one embodiments 34 to 37, wherein during the start-up stage, the start-up conditions comprise a start-up temperature $T^S$, wherein $T^S$ is the temperature of a heat transfer medium used for adjusting the temperature of the mixture in the epoxidation reaction zone, preferably by passing the heat transfer medium through a jacket of the epoxidation zone, wherein $T^S$ is preferably the temperature of the heat transfer medium prior to adjusting the temperature of the mixture, preferably the temperature of the heat transfer medium at the entrance of the jacket of the epoxidation zone.

39. The continuous process of embodiment 38, wherein at the beginning of the start-up stage, $T^S$ is in the range of from 30 to 40° C.

40. The continuous process of embodiment 38 or 39, wherein during the start-up stage, the average rate of change of $T^S$ is in the range of from −1 to 1 $K*h^{-1}$, preferably in the range of from −0.5 to 0.5 $K*h^{-1}$, more preferably in the range of from −0.1 to 0.1 $K*h^{-1}$.

41. The continuous process of any one of embodiments 38 to 40, wherein the epoxidation zone according to (ii) comprises a first epoxidation subzone consisting of one or more epoxidation reactors A, wherein, if the first epoxidation subzone comprises two or more epoxidation reactors A, the two or more epoxidation reactors A are arranged in parallel, and wherein in (ii), the liquid feed stream provided in (i) is passed into at least one of the epoxidation reactors A, wherein $T^S$ is the temperature of a heat transfer medium used for adjusting the temperature of the mixture in the first epoxidation subzone, preferably by passing the heat transfer medium through a jacket of the first epoxidation subzone, wherein $T^S$ is preferably the temperature of the heat transfer medium prior to adjusting the temperature of the mixture, preferably the temperature of the heat transfer medium at the entrance of the jacket of the first epoxidation subzone.

42. The continuous process of any one of embodiments 34 to 41, wherein the liquid stream according to (b) comprising hydrogen peroxide and being admixed to the liquid feed stream provided in (a) is an aqueous hydrogen peroxide stream having a hydrogen peroxide concentration in the range of from 25 to 75 weight-%, preferably in the range of from 30 to 50 weight-%, based on the total weight of the aqueous hydrogen peroxide stream.

43. The continuous process of embodiment 42, wherein the aqueous hydrogen peroxide stream comprises sodium Na+ at a molar ratio of sodium relative to hydrogen peroxide in the range of from $1\times10^{-6}$:1 to $250\times10^{-6}$, preferably from $5\times10^{-6}$:1 to $50\times10^{-6}$:1.

44. The continuous process of any one of embodiments 34 to 43, wherein during the start-up stage, the liquid feed stream passed in to the epoxidation zone contains ammonium $NH_4^+$ in an amount in the range of from 0 to 2 weight-ppm, preferably in the range of from 0 to 1 weight-ppm, based on the total weight of the liquid feed stream.

45. The continuous process of any one of embodiments 34 to 44, wherein the start-up stage consists of (a) and (b).

46. The continuous process of any one of embodiments 34 to 45, wherein during the start-up stage, the average rate of change of $a^S(Fo/H_2O_2)$ is greater than 0 $h^{-1}$.

47. The continuous process of embodiment 46, wherein the average rate of change of $a^S(Fo/H_2O_2)$ during step (b) of the start-up stage is in the range of from $1*10^{-5}$ to $1*10^{-3}$ $h^{-1}$, preferably in the range of from $5*10^{-5}$ to $1*10^{-4}$ $h^{-1}$.

48. The continuous process of embodiment 46, wherein the average rate of change of $a^S(Fo/H_2O_2)$ during step (b) of the start-up stage is in the range of from $1*10^{-6}$ to $5*10^{-5}$ $h^{-1}$, preferably in the range of from $5*10^{-6}$ to $1*10^{-5}$ $h^{-1}$.

49. The continuous process of any one of embodiments 34 to 48, preferably 46 to 48, wherein during the start-up stage, $a^S(Fo/H_2O_2)$ is changed stepwise.

50. The continuous process of any one of embodiments 34 to 49, wherein during the start-up stage, the maximum temperature of the liquid mixture in the epoxidation zone is in the range of from 70 to 100° C.

51. The continuous process of any one of embodiments 1 to 50, wherein the normal run stage lasts for at least 5,000 h, preferably at least 10,000 h, more preferably at least 15,000 h.

52. A method for increasing the propylene oxide selectivity of a catalyst comprising a titanium zeolite having framework type MWW in a continuous process for preparing propylene oxide, said continuous process for preparing propylene oxide comprising
  (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time is $a^N(Fo/H_2O_2)$;
  (ii) continuously passing the liquid feed stream provided in (i) into an epoxidation zone comprising the catalyst comprising a titanium zeolite having framework type MWW, and subjecting the liquid feed stream to epoxidation reaction conditions in the epoxidation zone, obtaining a reaction mixture comprising propylene oxide, acetonitrile, water, the formate salt, optionally propene, and optionally propane;
  said method for increasing the propylene oxide selectivity comprising decreasing $a^N(Fo/H_2O_2)$ in the course of said continuous process at otherwise constant epoxidation conditions.

53. The method of embodiment 52, wherein the formate salt is a potassium formate salt and the titanium zeolite having framework type MWW comprised in the catalyst according to (ii) contains titanium, calculated as elemental titanium, in an amount in the range of from 0.1 to 5 weight-%, preferably in the range of from 1 to 2 weight-%, based on the total weight of the titanium zeolite having framework type MWW and contains zinc, calculated as elemental zinc, in an amount in the range of from 0.1 to 5 weight-%, preferably in the range of from 1 to 2 weight-%, based on the total weight of the titanium zeolite having framework type MWW.

The present invention is further illustrated by the following reference examples, comparative examples, and examples.

EXAMPLES

Reference Example 1

Preparation of a Catalyst Comprising a Titanium Zeolite having Framework type MWW 1.1 Preparation of Boron Containing Zeolite of Structure MWW (BMWW)

A 2 m³ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox® AS40, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas. The white powder obtained (174.3 kg) contained 3.5 weight-% water. This white powder was then calcined at 650° C. in a rotary kiln to give 138.2 kg of boron containing zeolite of structure type MWW (BMWW) as a white powder.

1.2 Deboronation of BMWW with Water

A 5 m³ stirred tank reactor was loaded with 125 kg of the BMWW obtained according to the previous step 1.1 and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens/cm. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

1.3 Preparation of Titanium Containing Zeolite of Structure Type MWW (TiMWW)

A 2 m³ stirred tank reactor was first loaded with 111.2 kg of the spray-dried material from the previous step 1.2. In a separate 2 m³ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 m³ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m²/g.

1.4 Preparation of a Zinc Containing TiMWW (ZnTiMWW) by Impregnation a) In a vessel equipped with a reflux condenser, a solution of 981 kg deionized water and 6.0 kg zinc acetate dihydrate was prepared within 30 min. Under stirring (40 r.p.m.), 32.7 kg of the calcined Ti-MWW material obtained according to 1.3 above were suspended. Subsequently, the vessel was closed and the reflux condenser put into operation. The stirring rate was increased to 70 r.p.m.

b) In a vessel equipped with a reflux condenser, a solution of 585 kg deionized water and 3.58 kg zinc acetate dihydrate was prepared within 30 min. Under stirring (40 r.p.m.), 19.5 kg of the calcined Ti-MWW material obtained according to 1.3 above were suspended. Subsequently, the vessel was closed and the reflux condenser put into operation. The stirring rate was increased to 70 r.p.m.

In all batches a) and b), the mixture in the vessel was heated to 100° C. within 1 h and kept under reflux for 2h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. In total 297 kg of nitrogen dried filter cake were obtained. The thus dried Zn-impregnated TiMWW material (ZnTiMWW), had a Si content of 42 weight-%, a Ti content of 1.8 weight-%, a Zn content of 1.3 weight-.%.

From 297 kg of the mixture of the filter cake obtained above, an aqueous suspension was prepared with deionized water, the suspension having a solid content of 15 weight-%. This suspension was subjected to spray-drying in a spray-tower with the following spray-drying conditions:

apparatus used: spray tower with one nozzle
operation mode: nitrogen straight
configuration: dehumidifier-filter-scrubber
dosage: flexible-tube pump VF 10 (supplier: Verder)
nozzle with a diameter of 4 mm (supplier: Niro)
filter material: Nomex® needle-felt 10 m²

| | | Runtime/h | | | | |
|---|---|---|---|---|---|---|
| | | 0.5 | 1.5 | 2.5 | 3.5 | 4.5 |
| Flow rate gas/(kg/h) | | 550 | 550 | 550 | 550 | 550 |
| Temperature drying gas/ ° C. | spray tower (in) | 305 | 305 | 305 | 305 | 305 |
| | spray tower (out) | 151 | 151 | 151 | 151 | 151 |
| | Filter (in) | 140 | 137 | 130 | 127 | 126 |
| | Scrubber (in) | 110 | 110 | 110 | 108 | 105 |
| | Scrubber (out) | 14 | 14 | 15 | 15 | 15 |
| Differential pressure/ mbar | spray tower | 3.1 | 3 | 3 | 2.8 | 2.9 |
| | Filter | 1.7 | 1.7 | 1.8 | 1.8 | 2.1 |
| | Scrubber | 3.8 | 4.1 | 4.2 | 4.2 | 4.2 |
| Pressure/ mbar | spray tower | −103 | −1.2 | −0.9 | −0.9 | −1.1 |
| Nozzle gas | Flow rate kg/h | 23 | 23 | 23 | 23 | 23 |
| | Temperature/° C. | r.t.*⁾ | r.t.*⁾ | r.t.*⁾ | r.t.*⁾ | r.t.*⁾ |
| | Pressure/bar | 2.5 | 2.5 | 2.5 | 2.5 | 2.5 |
| Spray-dried product | Temperature/° C. | r.t.*⁾ | r.t.*⁾ | r.t.*⁾ | r.t.*⁾ | r.t.*⁾ |

*⁾room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 41 weight-%, and a TOC content of <0.5 weight-%. The spray-dried product was then subjected to calcination for 2 h at 650° C. under air in a rotary furnace, yielding 43.8 kg of calcined spray-dried ZnTiMWW. The calcined spray-dried material thus obtained had a Zn content of 1.3 weight-%, a Ti content of 1.8 weight-%, a Si content of 42.5 weight-%, and a C content of <0.1 weight-%. The bulk density of the calcined spray-dried ZnTiMWW was 90 g/l (gram/liter). The mesopores of the micropowder had an average pore diameter (4V/A) of 20.2 nm as determined by Hg porosimetry according to DIN 66133. The macropores of the micropowder had an average pore diameter (4V/A) of 67.6 nm as determined by Hg porosimetry according to DIN 66133. The micropores of the ZnTiMWW contained in the micropowder had an average pore diameter of 1.06 nm as determined by nitrogen adsorption according to DIN 66134 (Horward-Kawazoe method). The Dv10 value of the particles of the micropowder was 4.10 micrometers. The Dv50 value of the particles of the micropowder was 8.19 micrometers. The Dv90 value of the particles of the micropowder was 14.05 micrometers. The degree of crystallization determined via XRD was (77+/−10) %, the average crystallite size 35.0 nm +/−10%. It was found that the crystalline phase exhibits a pure MWW structure. No other crystalline titania phases such as anatase, rutile or brookite, or crystalline zinc silicate ($Zn_2SiO_4$) such as willemite could be detected.

1.5 Preparation of Moldings Containing ZnTiMWW and Silica Binder

Starting from the calcined spray-dried ZnTiMWW material obtained according to 1.4 above, a molding was prepared, dried, and calcined. Therefor, 12 batches were prepared, each starting from 3.5 kg of the calcined spray-dried ZnTiMWW material obtained above, 0.226 kg Walocel™

(Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 12 batches), 56 kg white strands with a diameter of 1.7 mm were obtained. 56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg. The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%. The mesopores of the micropowder had an average pore diameter (4V/A) of 20.9 nm as determined by Hg porosimetry according to DIN 66133. The macropores of the micropowder had an average pore diameter (4V/A) of 50.0 nm as determined by Hg porosimetry according to DIN 66133. The degree of crystallization determined via XRD was (70+/−10) %, the average crystallite size 32.5 nm+/−10%. The crush strength of the moldings as determined according to the method using a crush strength test machine Z2.5/TS1S was 4.4 N (standard deviation: 0.5 N). The minimum value found when testing the 10 samples was 3.5 N, the maximum value 5.1 N. In the $^{29}$SiMAS NMR, after the curve had been deconvolved by the proper Gaussian-Lorentzian line shapes, six peaks were clearly observed. The $Q^3/Q^4$ ratio was found to be 2.2. The total amount of adsorbed water as determined according to Reference Example 6 of the molding was 6.9 weight-%. The Langmuir surface are determined via nitrogen adsorption at 77 K according to DIN 66133 was 518 m$^2$/g, the mulitpoint BET specific surface area determined via nitrogen adsorption at 77 K according to DIN 66133 was 373 m$^2$/g. The total intrusion volume determined according to Hg porosimetry according to DIN 66133 was 1.3 ml/g (milliliter/gram), the respective total pore area 100.2 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Starting from the calcined strands, a post-treatment stage was performed as follows: 1,000 kg deionized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg. The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%. The mesopores of the micropowder had an average pore diameter (4V/A) of 22.1 nm as determined by Hg porosimetry according to DIN 66133. The macropores of the micropowder had an average pore diameter (4V/A) of 52,0 nm as determined by Hg porosimetry according to DIN 66133. The degree of crystallization determined via XRD was (69+/−10) %, the average crystallite size 30.5 nm+/−10%. The crush strength of the moldings as determined according to the method using a crush strength test machine Z2.5/TS1S was 13.7 N (standard deviation: 2.5 N). The minimum value found when testing the 10 samples was 10.2 N, the maximum value 17.6 N. In the $^{29}$Si MAS NMR, after the curve had been deconvolved by the proper Gaussian-Lorentzian line shapes, six peaks were clearly observed. The $Q^3/Q^4$ ratio was found to be 1.39. The total amount of adsorbed water of the molding was 6.9 weight-%. The intensity ratio of the infrared band in the region of (3746+/−20) cm$^{-1}$ attributed to the free silanol groups, relative to the infrared band in the region of 3688+/−20 cm$^{-1}$ attributed to vicinal silanol groups was smaller than 1.4. The Langmuir surface are determined via nitrogen adsorption at 77 K according to DIN 66133 was 421 m$^2$/g, the multipoint BET specific surface area determined via nitrogen adsorption at 77 K according t DIN 66133 was 303 m$^2$/g. The total intrusion volume determined according to Hg porosimetry according to DIN 66133 was 1.3 ml/g (milliliter/gram), the respective total pore area 98.7 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Reference Example 2

General Set-up of Epoxidation Process

A main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 17.5 kg of the ZnTiMWW catalyst moldings as prepared according to Reference Example 1 (post-treated moldings). Free space eventually remaining was filled with steatite spheres (diameter of 3 mm). The heat of reaction was removed by circulating a thermostatized heat transfer medium (water/glycol mixture) on the shell side in co-current to the feed. The flow rate of the heat transfer medium was adjusted so that the temperature difference between entrance and exit did not exceed 1° C. The reaction temperature referred to hereinbelow, also referred to as $T_r$, was defined as the temperature of the heat transfer medium entering the reactor shell. At the reactor exit, the pressure was controlled by a pressure regulator and kept constant at 20 bar(abs). The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100\times(1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d. The output stream (5) leaving the epoxidation unit A was passed through a heat exchanging unit. The stream leaving the heat exchanging unit (stream (6), S0) was fed to Epoxidation Unit B.

Epoxidation in a Finishing Reactor (Epoxidation Unit B): The finishing reactor B was a fixed bed reactor operated adiabatically. In this context, the term "adiabatic" refers to an operation mode according to which no active cooling is carried out and according to which the finishing reactor is suitably insulated in order to minimize heat losses. The finishing reactor B had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method. The effluent of the finishing reactor B, stream (6), was preferably depressurized into a flash drum, and both the liquid and the gas from this drum were fed to a light boiler separation column (distillation unit C).

Normal Run Stage

The main reactor A was fed from below with a liquid monophasic stream (1). Stream (1) was prepared by mixing four streams (2), (3), (3a) and (4). The temperature of stream (1) was in the range from 20 to 40° C. The streams were premixed at an absolute pressure of 23 bar. The liquid feed stream (1) consisted of one single liquid phase:

Stream (2) had a flow rate of 85 kg/h. At least 99.5 weight-% of stream (2) consisted of acetonitrile, propene and water. This stream (2) came from the bottoms of the acetonitrile recycle distillation unit (I).

Stream (3) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg). The aqueous hydrogen peroxide solution was supplied from a storage tank, allowing for a continuous feeding, and fed using a suitable metering pump.

Stream (3a) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream (S3a) was 370 g/h. Stream (3a) was thoroughly mixed with stream (3) before the combined stream was mixed with the stream resulting from mixing stream (2) and (4).

Stream (4) was a make-up stream of pure acetonitrile (chemical grade, from Ineos, purity about 99.9%, containing between 70-180 weight-ppm propionitrile, 5-20 weight-ppm acetamide and less than 100 weight-ppm water as impurities). Enough fresh acetonitrile was added to compensate for losses in the process. Under regular conditions, an average of from 100 to 150 g/h of make-up acetonitrile were added.

The experiments were performed in a continuous manner.

Start-Up Stage

1. First, an acetonitrile stream (69 kg/h (temperature: 30° C.; pressure: 26.5 bar(abs)) and a propene stream (12.9 kg/h; content of propane: 0.35 kg/h; temperature: 15° C.; pressure: 32 bar (abs)) are passed from below into the main reactor A. The temperature of the heat transfer medium was 30° C. The pressure of the reactor was 21 bar(abs).

2. Second, an aqueous potassium formate stream (500 g/h; concentration with respect to potassium formate: 2 weight-%; corresponds to 1,000 micromol potassium formate/mol hydrogen peroxide, see 3. below) was added to the acetonitrile stream.

3. In parallel to 2.), the hydrogen peroxide was added in the form of an aqueous hydrogen peroxide stream (concentration with respect to hydrogen peroxide: 40 weight-%). This addition was started using a stream of 3 kg/h. Then, for 2 h, the flow rate was increased for 1 kg/h every 15 minutes until the desired value of 15 kg/h was reached. During this period of time, the hydrogen peroxide conversion was always 100%. During this period of time, the maximum temperature in the reactor was at most 80° C.

After the start-up stage, when the normal run stage began, the values of $a^N(Fo/H_2O_2)$ and $T^N$ were varied as indicated in the comparative examples and the examples hereinbelow.

The reactor effluent stream downstream the pressure control valve was collected, weighed and analyzed. Organic components, with the exception of hydroperoxypropanols and oxygen were analyzed in two separate gas-chromatographs. The hydrogen peroxide content was determined colorimetrically using the titanyl sulfate method. The content of hydroperoxy-propanols, a mixture of 1-hydroperoxypropanol-2 and 2-hydroperoxypropanol-1, was determined by iodometrically measuring the total peroxide content and then subtracting the hydrogen peroxide content.

The selectivity for propylene oxide (PO) was determined relative to the hydrogen peroxide and was calculated as 100 times the ratio of moles of propylene oxide in the effluent stream divided by the moles of hydrogen peroxide in the feed stream. The selectivity for monopropylene glycol (MPG) was calculated as 100 times the ratio of moles of monopropylene glycol in the effluent divided by the moles of hydrogen peroxide in the feed. The selectivity for molecular oxygen given was calculated as 100 times the ratio of twice the number of moles of molecular oxygen in the effluent divided by the moles of hydrogen peroxide in the feed.

Reference Example 3

Characterization of the Catalyst

Reference Example 3.1

Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300RF mm; beam length 10.00 mm;

module MS17; shadowing 16.9%; dispersion model 3$$D; analysis model polydisperse correction none.

Reference Example 3.2

Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm $ZrO_2$ rotors. The $^{29}$Si MAS NMR spectra were collected at 79.5 MHz using a 1.9 µs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 3.3

Determination of the Crush Strength of the Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S ", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 3.4

$^{29}$Si Solid-State NMR Spectra Regarding $Q^3$ and $Q^4$ Structures

The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula 100*{[$a_1$+$a_2$]/[$a_4$+$a_5$+$a_6$]}/$a_3$. In this formula, $a_{i, i=1 \ldots 6}$ represents the area of the fitted peak to which this number was attributed.

Reference Example 3.5

Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 3.6

FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 cm$^{-1}$ at a resolution of 2 cm$^{-1}$. The obtained spectra are represented in a plot having on the x axis the wavenumber (cm$^{-1}$) and on the y axis the absorbance (arbitrary units, a.u.). For the quantitative determination of the peak heights and the ratio between these peaks a baseline correction was carried out. Changes in the 3000-3900 cm$^{-1}$ region were analyzed and for comparing multiple samples, as reference the band at 1880±5 cm$^{-1}$ was taken.

Reference Example 3.7

Determination of Crystallinity via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 4

Definition and Determination of the Octanol-water Partition Coefficient $K_{OW}$ The octanol-water partition coefficient $K_{OW}$ of a given compound is defined as the ratio of said compound's chemical concentration in the octanol phase relative to said compound's chemical concentration in the aqueous phase in a two-phase system of 1-octanol and water at a temperature of 25° C. The octanol-water partition coefficient $K_{OW}$ of a given compound is determined using the shake-flask method which consists of dissolving the compound in a volume of high-purity 1-octanol and deionized water (pre-mixed and calibrated for at least 24 h) and measuring the concentration of the compound in each the 1-octanol phase and the water phase by a sufficiently exact method, preferably via UV/VIS spectroscopy. This method is described in the OECD Guideline for the testing of chemicals, number 107, adopted on Jul. 27, 1995.

Reference Example 5

Preferred Downstream and Work-up Stages

Preferred conditions of parameters of preferred epoxidation reaction downstream stages and acetonitrile work-up stages described hereinabove are as follows:
Separation of Propylene Oxide from Stream S0 to Obtain Stream S1
a) Separation of light boilers from stream (6) (stream S0) to obtain a stream (8) (stream S01)

Stream (6) was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower. As a washing agent, part of the bottoms stream of distillation unit D (stream 11, about 20-30 kg/h) was taken off, cooled to 10° C. and introduced at the top of the column. Liquid and gaseous inlet streams were introduced the column at different points. The feed point of the liquid portion of stream (6) was above bubble tray 37; the gaseous portion of stream (6) was introduced into the column above bubble tray 28 (counted from the top). The gaseous stream (7) leaving the cooling means at the top of the column contained mainly propene, propane (which was contained as impurity in the polymer-grade propene used), oxygen formed as a by-product and small amounts of other light boilers (acetonitrile (1-2 volume-%), propionaldehyde (about 200 volume-ppm), acetone (about 100 volume-ppm, $H_2$ (about 400 volume-ppm), $CO_2$ (about 400 volume-ppm) and acetaldehyde (about 100 volume-ppm)), and was essentially free of propylene oxide (less than 300 volume-ppm). This top stream was sent to the flare for disposal. The bottom stream of the light boiler separation column (stream (8), that is stream S01,) having a temperature of 70° C., had a propene content of from 100 to 200 weight-ppm.
b) Separation of propylene oxide from stream (8) (stream S01) to obtain a stream S02

The stream S01 obtained according to a) above was introduced into a distillation column (distillation unit D) in order to separate propylene oxide from the stream S01. The column had a height of 50 m and a diameter of 220 mm and was equipped with a packing (Sulzer BX64) with a total packing length of 27.5 m divided into 8 beds with a length of 3060 mm each and two beds with a length of 1530 mm each. Between each bed intermediate flow distributors were installed. The column was operated at a top pressure of 750 mbar. The feed point of stream S01 was located below the fourth packing bed, counted from the top. The overhead stream of the column was condensed and partly returned to the column as reflux (reflux ratio approximately 5:1). The remainder (stream (9)), having a flow rate of 10.1 kg/h, was taken as overhead product and essentially consisted of propylene oxide having a purity of more than 99.9 weight-%. The bottoms evaporator was operated in such a way that the propylene oxide concentration in the bottoms stream was below 100 weight-ppm. The resulting temperature of the bottoms stream was about 69° C. The stream S02 was then divided in two. The major portion of it (stream (10), with a flow rate of ca. 85 kg/h) was sent to the next distillation column (distillation unit E). The remainder (stream (11), 20-30 kg/h) was cooled and recirculated to the top of the light boiler separation column (distillation unit C) as washing agent as described above in section a). This stream S02 had an acetonitrile content of about 80 weight-%, a propylene oxide content of less than 100 wt.-ppm, a water content of about 20 weight-%, a propene glycol content of about 0.1 weight-% and a hydroxypropanol content of about 0.1 weight-%.

c) Separation of light boiling compounds from stream (10) (stream S02) to obtain a stream (13) (stream S1)

The stream S02 obtained according to section b) above was introduced into a lights separation column (distillation unit E). This lights separation column had a height of 8 m and a nominal diameter of 150 mm and was equipped with 35 bubble trays. The column was operated at a top pressure of 2 bar, and the stream S02 was introduced above bubble tray number 7 (counted from the bottom). The overhead stream obtained (stream (12), flow rate about 1 kg/h) left the column with a temperature of from 40 to 45° C. and was not condensed as the column was operated with no internal reflux stream. Besides acetonitrile (6500 vol.-ppm), this overhead stream contained mainly nitrogen which was employed to keep the column operating pressure at a value of 2 bar) and small amounts of light boilers (acetaldehyde (900 vol.-ppm), oxygen (300 vol.-ppm), and propionaldehyde (320 vol.-ppm). This top stream was sent to the flare for disposal. The sump evaporator was operated by feeding it with a constant amount (5 kg/h) of saturated steam at a pressure of 16 bar. The bottom temperature of the column was 100° C. The bottoms stream, stream S1, mainly consisted of acetonitrile and water, the remainder being high boilers. This stream S1 had an acetonitrile content of about 80 weight-% and a water content of about 20 weight-%.

Dividing Stream S1 into Streams S2 and S3

The stream S1, flow rate 86 kg/h, obtained according to section c) above, was divided into two streams, streams S2 (stream (13a) according to FIG. 1) and S3 (stream 14 according to FIG. 1). Stream S2 had a flow rate of 84 kg/h and stream S3 had a flow rate of 2 kg/h. Stream S3, 2.3% of stream S1, was subjected to part stream distillation unit F (part stream distillation columns).

Part-Stream Distillation of Stream S1

The first fractionation unit, i.e. the first distillation column, F1, had a height of 9.5 m and a diameter of 85 mm and was equipped with 6.5 meters of metal structured Rombopak 9M packing installed in three identical beds. Above the first bed of the structured packing counted from the top, the stream S3 ((stream 14)) was introduced in the first distillation column. The temperature of the stream S3 stream was 60±3° C. The first distillation column was operated at a top pressure of about 1.4 bar and a bottoms temperature of 92±5° C. No reflux was applied. The amount of steam fed to the bottoms evaporator of the first fractionation unit was controlled in such a way that the concentration of acetonitrile in the bottoms was in the range of from 10 to 25 weight-%. The bottoms stream S4b (stream (15b), about 3% of the stream S3) was removed. This stream consisted mainly of water (72-85 weight-%) and acetonitrile (10-24 weight-%). The sum of all the analyzed high-boiling components (27 components) varied in the range of 2-10 weight-%. The top stream, vapor fraction stream S4a (stream 15a), having a temperature of from 85±3° C., was not condensed and passed to the bottom of the second fractionation unit, i.e. the second distillation column, F2. S4a entered F2 below the last bed of the structured packing counted from the top. F2 had a height of 9.5 m and a diameter of 85 mm and was equipped with 6.5 m of metal structured Rombopak 9M packing installed in 3 identical beds. The second distillation column was operated at a top pressure of about 1.25 bar and a bottoms temperature of 85±5° C. The top stream, vapor fraction stream S4c (stream (15c), at most 1% of the stream S4a), was fully condensed by an external overhead condenser (not shown in FIG. 2) and applied essentially completely to use the condensed, liquid stream as reflux to the second distillation column. The liquid bottoms stream S4 (stream 15), was removed and passed to the next step (recycling of the stream S4). The stream S4 had an acetonitrile content of about 80 weight-% and a water content of about 20 weight-%.

Recycling of the Stream S4 a) Preparing a Liquid Stream S5

Figure 2:
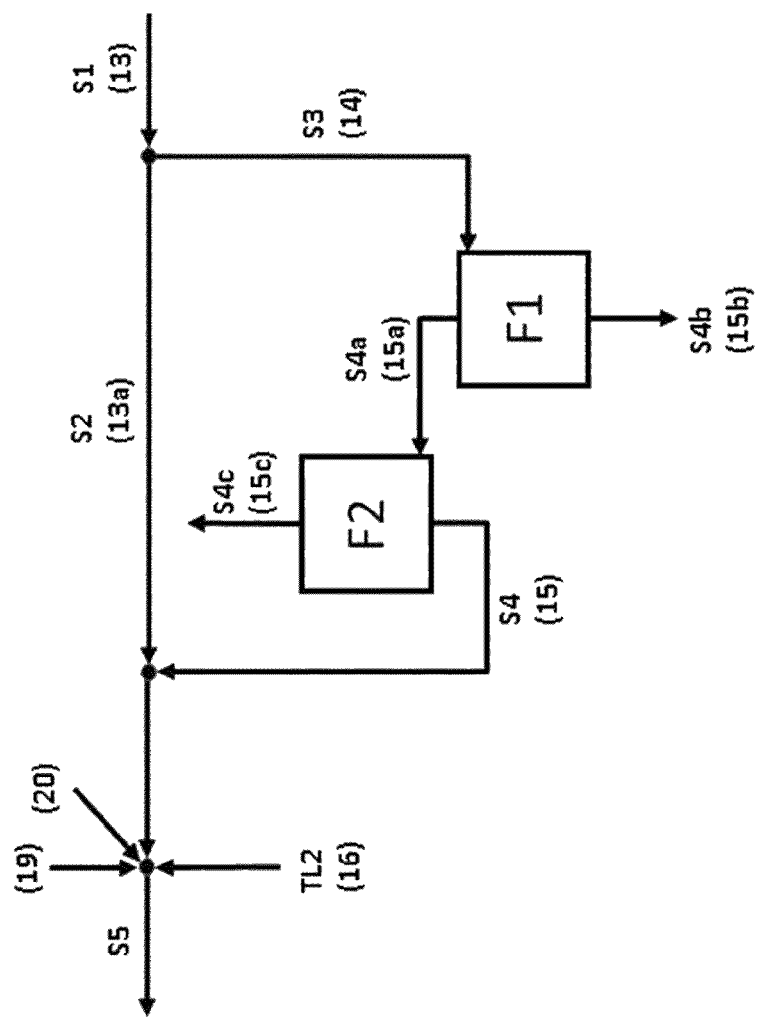

The stream S4, (stream 15 according to FIG. 1 and FIG. 2) was admixed with stream S2 (stream (13a) according to FIG. 1 and FIG. 2). Thus, the stream S4 was pumped back into the bulk process acetonitrile solvent stream. Mixing took place at a point downstream of where stream S3 was diverted from stream S1. This combined stream having a flow rate of 86 kg/h was mixed with a liquid stream P (referred to as stream (20) in FIG. 1 and FIG. 2) to obtain a stream S5. Stream P was fresh propene stream containing propane (polymer grade, purity>96 weight-%, liquefied under pressure, feed rate: 10.9 kg/h). In order to obtain the stream S5, the combined stream of S2 and S4 was further mixed with two other streams: the first one of these streams is stream (16) according to FIG. 1, said stream being obtained from the top of the distillation unit H. The second one of these streams is stream (19) according to FIG. 1, said stream being obtained from the acetonitrile recovery unit I. Both streams (16) and (19) are described in detail hereinunder.

b) Adjusting the Temperature of Stream S5 and Separating Liquid Phases L1 and L2

The stream S5 having a flow rate of 130 kg/h±10 kg/h was then fed to a mixer-settler unit operated at 18 bar and a temperature in the range of 15±5° C. The settler tank had a volume of 5.3 liters. Two liquid phases L1 and L2 were obtained, an aqueous phase L2 and an organic phase L1. The upper organic phase L1 was removed from the settler tank as stream (17), the lower aqueous phase L2 was removed from the settler tank as stream (18). The stream (17) had a flow rate in the range of 110 kg/h±11 kg/h. The stream (17) then was passed to the acetonitrile recycle unit I, the stream (18) was passed to the acetonitrile recovery unit H from which the stream (16) mentioned above was obtained. The stream (17) thus obtained had an acetonitrile content of about 45-51 weight-%, a propene content of about 49-55 weight-% and a water content of about 2 to 5 weight-%. The stream (18) thus obtained had an acetonitrile content of about 19-21 weight-%, a water content of about 79-81 weight-% and a propene content of less than 0.5 weight-%.

c) Acetonitrile Recovery (Acetonitrile Recovery Unit H)

In order to recycle as much solvent as possible, and in order to minimize acetonitrile losses, the stream (18) was introduced into a distillation column from which the stream (16), also referred to as stream TL2, was obtained as top stream which in turn was recycled into the solvent stream as described above. For this purpose, a distillation column with a height of 9.5 m and a diameter of 100 mm, equipped with 50 bubble trays was used. The column was operated at a top pressure of 1.5 bar with a reflux ratio of 1:4. Stream (18) was fed to the column above bubble tray 26 (counted from the bottom). The bottoms temperature was about 113° C., and the bottoms product consists mainly of water containing high boiling by-products. A typical composition of the bottoms stream was as follows (weight-% given in parenthesis): water (>99.0), propene glycol (0.5), acetonitrile (at most 0.001), dipropylene glycol (0.06), acetamide (0.01), acetic acid (0.03), TOC (2.4)). After optional metering and analyzing, this stream was discarded.

The overhead product (stream (16)=stream TL2) had the following typical composition ranges (weight-% given in parenthesis): acetonitrile (75-80), water (15-20), low boilers (e.g. propene, 1). As described above stream (16) is recycled to the feed stream which is passed to the mixer-settler unit.

d) Acetonitrile Recycling (Acetonitrile Recycling Unit I)

For acetonitrile recycle, the stream (17) obtained from the mixer-settler unit G was introduced into a distillation column with a height of 10 m and a nominal diameter of 200 mm, equipped with 40 bubble trays. The column was operated at a top pressure of 18 bar with a reflux ratio of 1:4. Stream (17) was fed to the column above bubble tray 26 (counted from the top). The top product (stream (19)), also referred to as stream TL1, containing mainly propene (ca. 97 vol.-%) with small amounts of propane (ca. 1-3 vol.-%) was returned to the feed of the mixer-settler unit G as described above. Thus, excess propene was removed from steam (17) and recycled. The bottoms stream (stream (2), also referred to as stream BL1), had a temperature in the range of from 106 to 110° C. The precise operation parameters of the column, like energy input in the sump, are adjusted in such a way that the amount of propene returned to the reactor with stream (2) is in a range such that the molar ratio of propene to hydrogen peroxide in stream (1) was about 1:1.43. For the above mentioned feed rate of 15 kg/h of aqueous hydrogen peroxide, this means that the conditions needed to be adjusted such that the flow rate of propene in stream (2) was about 9.7 kg/h. Prior to feeding stream (2) to the main epoxidation reactor A, acetonitrile (stream (4), chemical grade, from Ineos, purity about 99.9%, containing between 70-180 weight-ppm propionitrile, 5-20 weight-ppm acetamide and <100 weight-ppm water as impurities) was optionally added to compensate for possible solvent losses. The exact amount of additionally added acetonitrile required depended on the losses in exit streams and in by-products but also on the number of samples taken for analytics. A typical amount of additionally added acetonitrile for the above-described process design may be in the range of from 100 to 150 g/h.

Comparative Example 1

Epoxidation Process with an Average Rate of Change of $a^N(Fo/H_2O_2)$ of 0 $h^{-1}$ An epoxidation reaction was carried out as described hereinabove in Reference Example 2. After the start-up stage of 100 h and, thus, at the beginning of the normal run stage, $a^N(Fo/H_2O_2)$ had a value of 1,000 micromol/mol. This value was not changed during the normal run stage. In order to achieve an average hydrogen peroxide conversion of more than 99.5%, the temperature $T^N$ was increased at a constant ramp of 0.05 K/d. At the end of the normal run stage, after a total time on stream of 3000 h, $T^N$ had a value of 35.8° C. The following selectivities were observed:

TABLE 1

| Results of Comparative Example 1 | | | | | |
|---|---|---|---|---|---|
| $a^N(Fo/H_2O_2)/$ | Time on | | Selectivities/% | | |
| µmol/mol | stream/h | $T^N/°$ C. | PO | MPG | $O_2$ |
| Start-Up 1000 | 0-100 | 30 | 97.2 | 0.7 | 1.3 |
| Normal Run 1000 | 100-500 | 30.8 | 97.1 | 0.7 | 1.4 |
| 1000 | 500-1000 | 31.8 | 96.9 | 1.1 | 1.5 |
| 1000 | 1000-3000 | 35.8 | 96.3 | 1.3 | 1.9 |

It was observed that when keeping $a^N(Fo/H_2O_2)$ constant after the start-up stage, during the normal run stage, the selectivity with regard to propylene oxide as valuable product decreased from an initial value of 97.2% to a final value of 96.3% whereas the selectivities of undesired by-products (MPG and $O_2$) increased.

Example 1

Epoxidation Process with an Average Rate of Change of $a^N(Fo/H_2O_2)$ of Less than 0 $h^{-1}$ An epoxidation reaction was carried out as described hereinabove in Reference Example 2. After the start-up stage of 100 h and, thus, at the beginning of the normal run stage, $a^N(Fo/H_2O_2)$ had a value of 1,000 micromol/mol. This value was decreased during the normal run stage as indicated in Table 2. During the normal run stage, the average hydrogen peroxide conversion was more than 99.5%. The temperature TN was varied as indicated in Table 2 below. The following selectivities were observed:

TABLE 2

| Results of Example 1 | | | | | |
|---|---|---|---|---|---|
| $a^N(Fo/H_2O_2)/$ | Time on | | Selectivities/% | | |
| µmol/mol | stream/h | $T^N/°$ C. | PO | MPG | $O_2$ |
| Start-Up 1000 | 0-100 | 30 | 97.2 | 0.7 | 1.3 |
| Normal Run 1000 | 100-544 | 30 | 97.2 | 0.6 | 1.2 |
| 750 | 544-1532 | 30 | 97.4 | 0.4 | 1.0 |
| 500 | 1532-2244 | 30 | 97.6 | 0.3 | 0.8 |
| 300 | 2244-3722 | 30 | 97.7 | 0.1 | 0.6 |
| 200 | 3722-4326 | 30 | 97.2 | 0.6 | 1.2 |
| 200 | 4326-5012 | 35 | 97.4 | 0.4 | 1.0 |

It was observed that decreasing $a^N(Fo/H_2O_2)$ in the course of the normal run stage, the selectivity with regard to propylene oxide as valuable product increased from an initial value of 97.2% to a final value of 97.4% whereas the selectivities of undesired by-products (MPG and O2) decreased.

Example 2

Epoxidation Process with an Average Rate of Change of $a^N(Fo/H_2O_2)$ of less than 0 $h^{-1}$ An epoxidation reaction was carried out as described hereinabove in Reference Example 2. After the start-up stage of 100 h and, thus, at the beginning of the normal run stage, $a^N(Fo/H_2O_2)$ had a value of 1,000 micromol/mol. This value was decreased during the normal run stage as indicated in Table 2. During the normal run stage, the average hydrogen peroxide conversion was more than 99.5%. The temperature $T^N$ was varied as indicated in Table 3 below. The following selectivities were observed:

TABLE 3

Results of Example 2

| | $a^N(Fo/H_2O_2)$/ micromol/mol | Time on stream/h | $T^N$/° C. | Selectivities/% | | |
|---|---|---|---|---|---|---|
| | | | | PO | MPG | $O_2$ |
| Start-Up | 1000 | 0-100 | 30 | 97.2 | 0.7 | 1.3 |
| Normal Run | 1000 | 100-672 | 30 | 97.2 | 0.6 | 1.2 |
| | 500 | 672-1034 | 30 | 97.6 | 0.3 | 1.0 |
| | 500 | 1034-1714 | 35 | 97.3 | 0.4 | 1.3 |
| | 300 | 1714-2918 | 35 | 97.6 | 0.2 | 1.1 |
| | 200 | 2918-4824 | 35 | 97.7 | 0.2 | 0.8 |

It was observed that decreasing $a^N(Fo/H_2O_2)$ in the course of the normal run stage, the selectivity with regard to propylene oxide as valuable product increased from an initial value of 97.2% to a final value of 97.4% whereas the selectivities of undesired by-products (MPG and $O_2$) decreased.

SHORT DESCRIPTION OF THE FIGURES

FIG. 1 shows a block diagram of the process according to Reference Example 2. In FIG. 1, the letters and numbers have the following meanings:
A epoxidation unit A
B epoxidation unit B
C distillation unit
D distillation unit
E distillation unit
F part stream distillation unit
G mixer-settler unit
H acetonitrile recovery unit
I acetonitrile recycle unit
(1)-(20) streams according to a specifically preferred process as described in the examples
S0, S01, S02, S1, S2, S3, S4, S4b, S5, L1, L2, TL1, TL2, TL2, BL2
streams according to a preferred process as described in the general description and the examples
FIG. 2 shows a block diagram the part stream distillation F of FIG. 1 unit in detail. In FIG. 2, the letters and numbers have the following meanings:
F1 first fractionation unit of the part stream distillation unit F
F2 second fractionation unit of the part stream distillation unit F
(13), (13a), (14), (15), (15a), (15b), (15c), (16), (19), (20) streams according to a specifically preferred process as described in the examples
S1, S2, S3, S4, S4a, S4b, S4c, S5, TL2
streams according to a preferred process as described in the general description and the examples

CITED LITERATURE

WO 2011/006990 A
Ullmann's Encyclopedia of Industrial Chemistry, $5^{th}$ edition, volume A 13 (1989) pages 443-466
EP 1 122 249 A1
EP 0 427 062 A2
U.S. Pat. No. 5,194,675

The invention claimed is:

1. A continuous process for preparing propylene oxide comprising a start-up stage and a normal run stage, wherein the normal run stage comprises:
   (i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time during the normal run stage is $a^N(Fo/H_2O_2)$;
   (ii) continuously passing the liquid feed stream provided in (i) into an epoxidation zone comprising a catalyst comprising a titanium zeolite having framework MWW, and subjecting the liquid feed stream to epoxidation reaction conditions in the epoxidation zone, obtaining a reaction mixture comprising propylene oxide, acetonitrile, water, the formate salt, optionally propene, and optionally propane; and
   (iii) continuously removing an effluent stream from the epoxidation zone, the effluent stream comprising propylene oxide, acetonitrile, water, at least a portion of the formate salt, optionally propene, and optionally propane;
   wherein the normal run stage is characterized in an average rate of change of $a^N(Fo/H_2O_2)$ of less than 0 $h^{-1}$.

2. The continuous process of claim 1, wherein the average rate of change of $a^N(Fo/H_2O_2)$ ranges from $-10^{-10}$ to $-10^{-6}$ $h^{-1}$.

3. The continuous process of claim 1, wherein at the beginning of the normal run stage, $a^N(Fo/H_2O_2)$ ranges from $1.0*10^{-4}$ to $1.0*10^{-2}$.

4. The continuous process of claim 1, wherein:
   during the normal run stage, the epoxidation conditions according to (ii) comprise an epoxidation temperature $T^N$;
   during the normal run stage, the average rate of change of $T^N$ ranges from 0 to 50 $K*h^{-1}$; and
   $T^N$ is the temperature of a heat transfer medium used for adjusting the temperature of the reaction mixture in the epoxidation reaction zone according to (ii).

5. The continuous process of claim 4, wherein:
   during the initial stage of the normal run stage, the average rate of change of $T^N$ ranges from 0 to 0.5 $K*h^{-1}$; and
   after said initial stage, when $a^N(Fo/H_2O_2)$ ranges from 40 to 60% of $a^N(Fo/H_2O_2)$ at the beginning of the normal run stage, $T^N$ is increased by at least 0.1° C.

6. The continuous process of claim 4, wherein during the normal run stage, $T^N$ ranges from 20 to 70° C.

7. The continuous process of claim 1, wherein:
   during the normal run stage, the epoxidation conditions according to (ii) comprise a hydrogen peroxide conversion $c^N(H_2O_2)$;
   the average rate of change of $c^N(H_2O_2)$ ranges from $-1.0*10^{-3}$ to $1.0*10^{-3}$%-points*$h^{-1}$; and
   $c^N(H_2O_2)$ is defined as the molar amount of hydrogen peroxide comprised in the effluent stream removed in (iii) relative to the molar amount of hydrogen peroxide comprised in the liquid feed stream provided in (i) at a given point of time during the normal run stage.

8. The continuous process of claim 7, wherein during the normal run stage, $c^N(H_2O_2)$ ranges from 99.5 to 100%.

9. The continuous process of claim 1, wherein the formate salt according to (i) consists of a potassium formate salt.

10. The continuous process of claim 1, wherein:
during the normal run stage, the epoxidation conditions according to (ii) comprise an epoxidation reaction pressure ranging from 14 to 100 bar; and
the epoxidation reaction pressure is defined as the absolute pressure at the exit of the epoxidation zone.

11. The continuous process of claim 1, wherein:
during the normal run stage, the epoxidation conditions according to (ii) comprise a catalyst loading ranging from 0.05 to 1.25 $h^{-1}$; and
the catalyst loading is defined as the ratio of the mass flow rate in kg/h of hydrogen peroxide contained in liquid feed stream provided in (i) relative to the amount in kg of catalyst comprising a titanium zeolite having framework MWW comprised in the epoxidation zone according to (ii).

12. The continuous process of claim 1, wherein the titanium zeolite having framework MWW comprised in the catalyst according to (ii) contains titanium, calculated as elemental titanium, in an amount ranging from 0.1 to 5 weight-%, based on the total weight of the titanium zeolite having framework MWW.

13. The continuous process of claim 1, wherein the titanium zeolite having framework MWW comprised in the catalyst according to (ii) contains titanium, calculated as elemental titanium, in an amount ranges from 0.1 to 5 weight-%, based on the total weight of the titanium zeolite having framework MWW, and contains zinc, calculated as elemental zinc, in an amount ranging from 0.1 to 5 weight-%, based on the total weight of the titanium zeolite having framework MWW.

14. The continuous process of claim 1, wherein during the normal run stage, the liquid feed stream provided in (i) comprises:
the acetonitrile in an amount ranging from 60 to 75 weight-%, based on the total weight of the liquid feed stream;
the hydrogen peroxide in an amount ranging from 6 to 10 weight-%, based on the total weight of the liquid feed stream;
the water at a molar ratio of water relative to acetonitrile ranging from 1:50 to 1:4;
the propene at a molar ratio of propene relative to hydrogen peroxide comprised in the liquid feed stream ranging from 1:1 to 1.6:1, and
optionally the propane at a molar ratio of propane relative to the sum of propene and propane ranging from 0.0001:1 to 0.15:1;
wherein at least 95 weight-% of the liquid feed stream provided in (i) consist of propene, hydrogen peroxide, acetonitrile, the formate salt, water and optionally propane.

15. The continuous process of claim 1, comprising a start-up stage prior to the normal run stage, wherein the start-up stage comprises:
(a) continuously providing a liquid feed stream comprising propene, acetonitrile, and optionally propane and continuously passing said liquid feed stream under start-up conditions for a period of time $t_1$ into the epoxidation zone comprising the catalyst comprising a titanium zeolite having framework MWW;
wherein after the period of time $t_1$, the start-up stage further comprises:
(b) continuously providing a liquid feed stream comprising hydrogen peroxide, admixing said liquid feed stream to the liquid feed stream provided in (a) obtaining a liquid feed stream comprising hydrogen peroxide, propene, acetonitrile, and optionally propane, and continuously passing said liquid feed stream under start-up conditions for a period of time $t_2$ into the epoxidation zone comprising the catalyst comprising a titanium zeolite having framework structure MWW,
wherein:
the liquid feed stream according to (b) comprises the formate salt, wherein the molar amount of the formate salt relative to the molar amount of hydrogen peroxide at a given point of time during step (b) of the start-up stage is $a^S(Fo/H_2O_2)$; and
after the period of time $t_2$, the normal run stage begins and $a^S(Fo/H_2O_2)$ is $a^N(Fo/H_2O_2)$ at the beginning of the normal run stage.

16. The continuous process of claim 15, wherein at least 98 weight-% of the liquid feed stream provided in (a) consist of propene, acetonitrile, and optionally propane, wherein the liquid feed stream according to (a) comprises hydrogen peroxide in an amount ranging from 0 to 0.01 weight-%, based on the total weight of the liquid feed stream, and wherein the liquid feed stream according to (a) comprises the formate salt in an amount ranging from 0 to 0.01 weight-%, based on the total weight of the liquid feed stream.

17. The continuous process of claim 15, wherein during the start-up stage, the start-up conditions comprise a start-up temperature $T^S$, wherein $T^S$ is the temperature of a heat transfer medium used for adjusting the temperature of the mixture in the epoxidation reaction zone, wherein at the beginning of the start-up stage, $T^S$ ranges from 30 to 40° C., and wherein during the start-up stage, the average rate of change of $T^S$ ranges from −1 to 1 $K*h^{-1}$.

18. The continuous process of claim 15, wherein during the start-up stage, the average rate of change of $a^S(Fo/H_2O_2)$ is greater than 0 $h^{-1}$.

19. The continuous process of claim 15, wherein during the start-up stage, the maximum temperature of the liquid mixture in the epoxidation zone ranges from 70 to 100° C.

20. A method for increasing the propylene oxide selectivity of a catalyst comprising a titanium zeolite having framework MWW in a continuous process for preparing propylene oxide, said continuous process for preparing propylene oxide comprising:
(i) continuously providing a liquid feed stream comprising propene, hydrogen peroxide, acetonitrile, a formate salt, water and optionally propane, wherein in the liquid feed stream, the molar amount of the formate salt relative to the molar amount of hydrogen peroxide at a given point of time is $a^N(Fo/H_2O_2)$; and
(ii) continuously passing the liquid feed stream provided in (i) into an epoxidation zone comprising the catalyst comprising a titanium zeolite having framework MWW, and subjecting the liquid feed stream to epoxidation reaction conditions in the epoxidation zone, obtaining a reaction mixture comprising propylene oxide, acetonitrile, water, the formate salt, optionally propene, and optionally propane;
said method for increasing the propylene oxide selectivity comprising decreasing $a^N(Fo/H_2O_2)$ in the course of said continuous process at otherwise constant epoxidation conditions, wherein the formate salt is a potassium formate salt and the titanium zeolite having framework MWW comprised in the catalyst according to (ii) contains titanium, calculated as elemental titanium, in an amount ranging from 0.1 to 5 weight-%, based on the total weight of the titanium zeolite having framework MWW, and contains zinc, calculated as elemental zinc, in an amount ranging from 0.1 to 5 weight-%, based on the total weight of the titanium zeolite having framework MWW.

\* \* \* \* \*

UNITED STATES PATENT AND TRADEMARK OFFICE
CERTIFICATE OF CORRECTION

PATENT NO. : 10,544,115 B2
APPLICATION NO. : 16/076600
DATED : January 28, 2020
INVENTOR(S) : Dominic Riedel et al.

It is certified that error appears in the above-identified patent and that said Letters Patent is hereby corrected as shown below:

In the Specification

Column 1, Line 20, delete "possible" and insert --possible.--.

Column 3, Line 47, delete "$0^{-1}$ ." and insert --0 $h^{-1}$.--.

Column 4, Line 9, delete "$0^{-1}$" and insert --0 $h^{-1}$--;
Line 33, delete "-$10^{-10}$ to" and insert --$10^{-10}$ to--.

Column 9, Line 32, delete "wherein wherein" an insert --wherein--;
Line 44, delete "25to" and insert --25 to--.

Column 12, Line 12, delete "of of" and insert --of--;
Line 38, delete "the the" and insert --the--.

Column 16, Line 9, delete "20 cm⁻ is" and insert --20 $cm^{-1}$ is--;
Line 41, delete "the the" and insert --the--.

Column 18, Line 10, delete "$Na^+$at" and insert --$Na^+$ at--.

Column 21, Line 31, delete "1.1." and insert --1:1.--.

Column 25, Line 43, delete "$0^{-1}$." and insert --O $h^{-1}$.l--.

Column 30, Line 58, delete "Na+at" and insert --$Na^+$ at--.

Column 35, Line 40, delete "$^{29}$SiMAS NMR," and insert --$^{29}$Si MAS NMR,--;
Line 47, delete "mulitpoint" and insert --multipoint--;
Line 58, delete "deioinized" and insert --deionized--.

Signed and Sealed this
Twenty-sixth Day of May, 2020

Andrei Iancu
*Director of the United States Patent and Trademark Office*

CERTIFICATE OF CORRECTION (continued)
U.S. Pat. No. 10,544,115 B2

Column 43, Line 45, delete "(13a" and insert --13a--.

Column 46, Line 34, delete "TN" and insert --$T^N$--.

In the Claims

Column 49, Line 8, Claim 11, delete "nm" and insert --run--.